United States Patent [19]

Stefanchik et al.

[11] Patent Number: 5,171,249
[45] Date of Patent: Dec. 15, 1992

[54] ENDOSCOPIC MULTIPLE LIGATING CLIP APPLIER

[75] Inventors: David Stefanchik, Mason; Jerome E. Reckelhoff; Rudolph H. Nobis, both of Cincinnati, all of Ohio; Michael A. Murray, Bellevue, Ky.; John E. Burbank, Ridgefield, Conn.

[73] Assignee: Ethicon, Inc., Somerville, N.J.

[21] Appl. No.: 680,215

[22] Filed: Apr. 4, 1991

[51] Int. Cl.$^5$ ............................................. A61B 17/00
[52] U.S. Cl. .................................. 606/142; 606/143; 604/167
[58] Field of Search ................. 606/143, 46, 207, 142, 606/205; 81/420, 419, 418; 604/167; 128/4

[56] References Cited

U.S. PATENT DOCUMENTS

| | | | |
|---|---|---|---|
| 3,777,538 | 12/1973 | Weatherly et al. | 72/410 |
| 3,870,048 | 3/1975 | Yoon . | |
| 3,955,581 | 5/1976 | Spasiano et al. . | |
| 4,027,510 | 6/1977 | Hiltebrandt | 72/37 |
| 4,038,987 | 8/1977 | Komiya . | |
| 4,101,063 | 7/1978 | Kapitanov et al. | 227/19 |
| 4,152,920 | 5/1979 | Green | 72/410 |
| 4,169,476 | 10/1979 | Hiltebrandt . | |
| 4,185,762 | 1/1980 | Froehlich | 227/138 |
| 4,196,836 | 4/1980 | Becht | 227/110 |
| 4,226,239 | 10/1980 | Polk et al. . | |
| 4,226,242 | 10/1980 | Jarvik . | |
| 4,230,116 | 10/1980 | Watson . | |
| 4,242,902 | 1/1981 | Green | 72/410 |
| 4,246,903 | 1/1981 | Larkin | 606/143 |
| 4,257,219 | 3/1981 | Goltner et al. . | |
| 4,273,129 | 6/1981 | Boebel . | |
| 4,296,751 | 10/1981 | Blake, III et al. . | |
| 4,299,224 | 11/1981 | Noiles . | |
| 4,316,468 | 2/1982 | Klieman et al. . | |
| 4,325,376 | 4/1982 | Klieman et al. . | |
| 4,372,316 | 2/1983 | Blake, III et al. . | |
| 4,374,523 | 2/1983 | Yoon . | |
| 4,412,539 | 11/1983 | Jarvik . | |
| 4,425,915 | 1/1984 | Ivanov . | |
| 4,430,997 | 2/1984 | DiGiovanni et al. . | |
| 4,452,357 | 6/1984 | Klieman et al. | 206/339 |
| 4,452,376 | 6/1984 | Klieman et al. | 221/198 |
| 4,509,518 | 4/1985 | McGarry et al. | 606/143 |
| 4,522,207 | 6/1985 | Klieman et al. . | |
| 4,534,351 | 8/1985 | Rothfuss et al. . | |
| 4,549,544 | 10/1985 | Favaron . | |
| 4,572,183 | 2/1986 | Juska . | |
| 4,576,166 | 3/1986 | Montgomery et al. . | |
| 4,598,711 | 7/1986 | Deniega . | |
| 4,611,595 | 9/1986 | Klieman et al. . | |
| 4,616,650 | 10/1986 | Green et al. | 606/143 |
| 4,624,254 | 11/1986 | McGarry et al. . | |

(List continued on next page.)

FOREIGN PATENT DOCUMENTS

EP409 569 1/1991 European Pat. Off. .
WO8910094 11/1989 PCT Int'l Appl. .

OTHER PUBLICATIONS

Auto Suture Premium Surgiclip Titanium Disposable Automatic Clip Appliers, U.S. Surgical Corporation, Copyright 1988.
New Surgical Procedure for Indirect Hernias, Innovative Surgical Devices, Inc.

Primary Examiner—Stephen C. Pellegrino
Assistant Examiner—Jeffrey A. Schmidt
Attorney, Agent, or Firm—Paul A. Coletti

[57] ABSTRACT

An endoscopic clip applying system as described which contains a venting system and a clip applying support system which prevents closure of the mechanism before firing. Also, the system ensures proper loading of the clips and prevents them from falling out during loading. Further, the system describes an easily manufacturable, positively opening system which has minimized size requirements. Furthermore, a lock-out mechanism is provided so that the mechanism may not be inadvertently fired. The shaft resists excessive torque as well as holds the clip in place during firing. There are provisions for sealant and non back-up of the clips, as well as features which make the clip properly placed for closure.

44 Claims, 14 Drawing Sheets

U.S PATENT DOCUMENTS

| | | | |
|---|---|---|---|
| 4,646,740 | 3/1987 | Peters et al. | |
| 4,662,373 | 5/1987 | Montgomery et al. | |
| 4,674,504 | 6/1987 | Klieman et al. | |
| 4,691,853 | 9/1987 | Storace | 227/19 |
| 4,712,549 | 12/1987 | Peters et al. | 606/143 |
| 4,784,137 | 11/1988 | Kulik et al. | |
| 4,841,888 | 6/1989 | Mills et al. | 112/169 |
| 4,944,443 | 7/1990 | Oddson et al. | 227/19 |
| 5,000,745 | 3/1991 | Guest et al. | 604/167 |
| 5,009,391 | 4/1991 | Steigerwald | 604/167 |
| 5,030,226 | 7/1991 | Green et al. | 606/158 |
| 5,049,152 | 9/1991 | Simon et al. | 606/142 |
| 5,084,057 | 1/1992 | Green et al. | 606/142 |
| 5,100,418 | 3/1992 | Yoon et al. | 606/139 |
| 5,100,420 | 3/1992 | Green et al. | 606/143 |
| 5,104,394 | 4/1992 | Knoepfler | 606/143 |

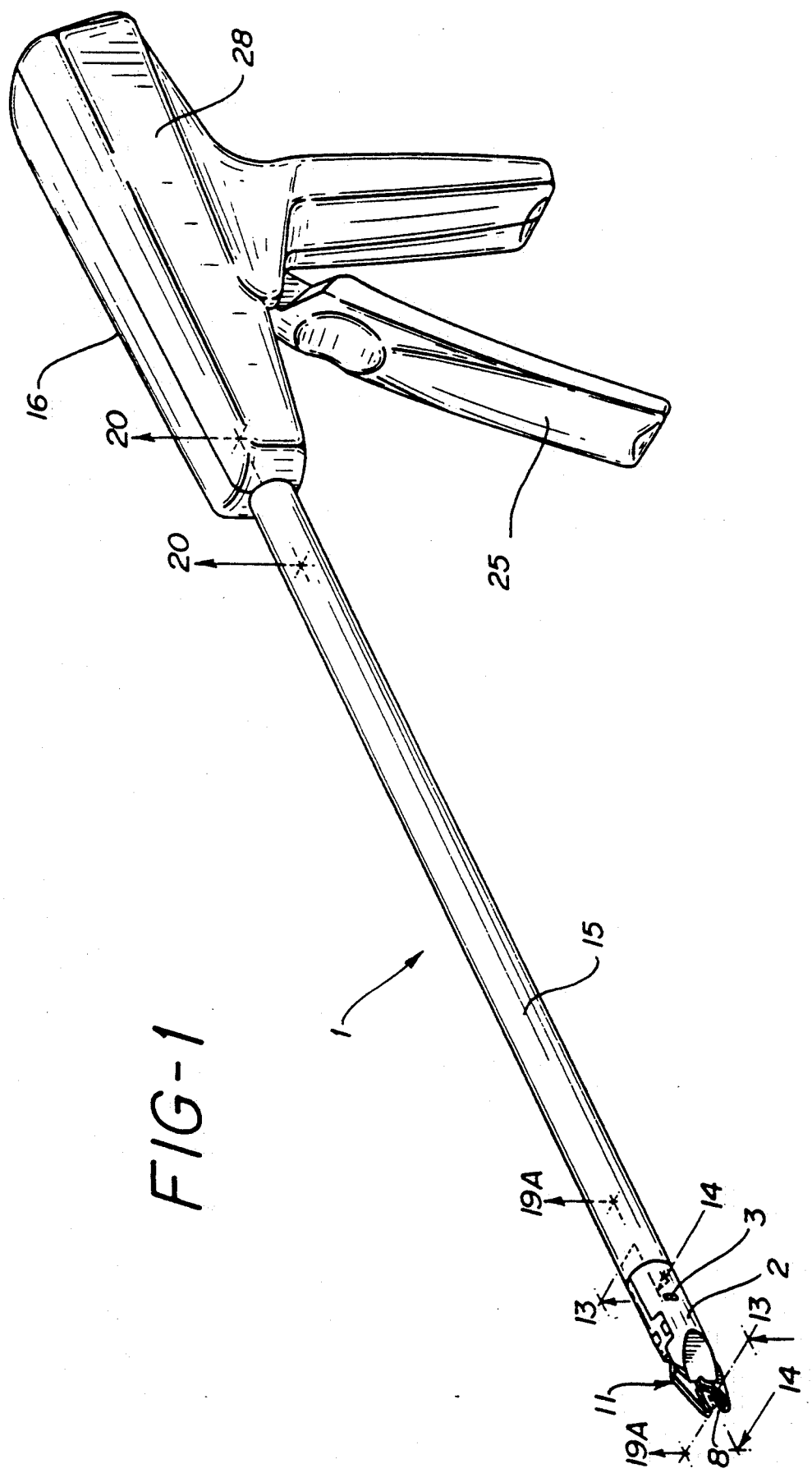

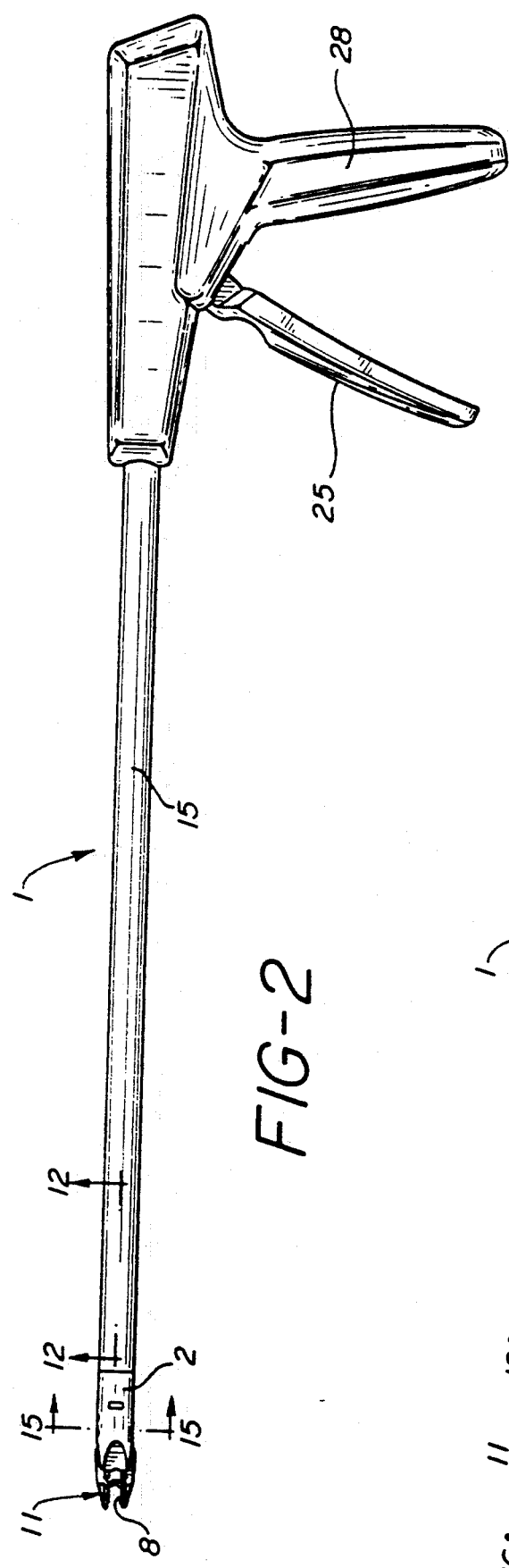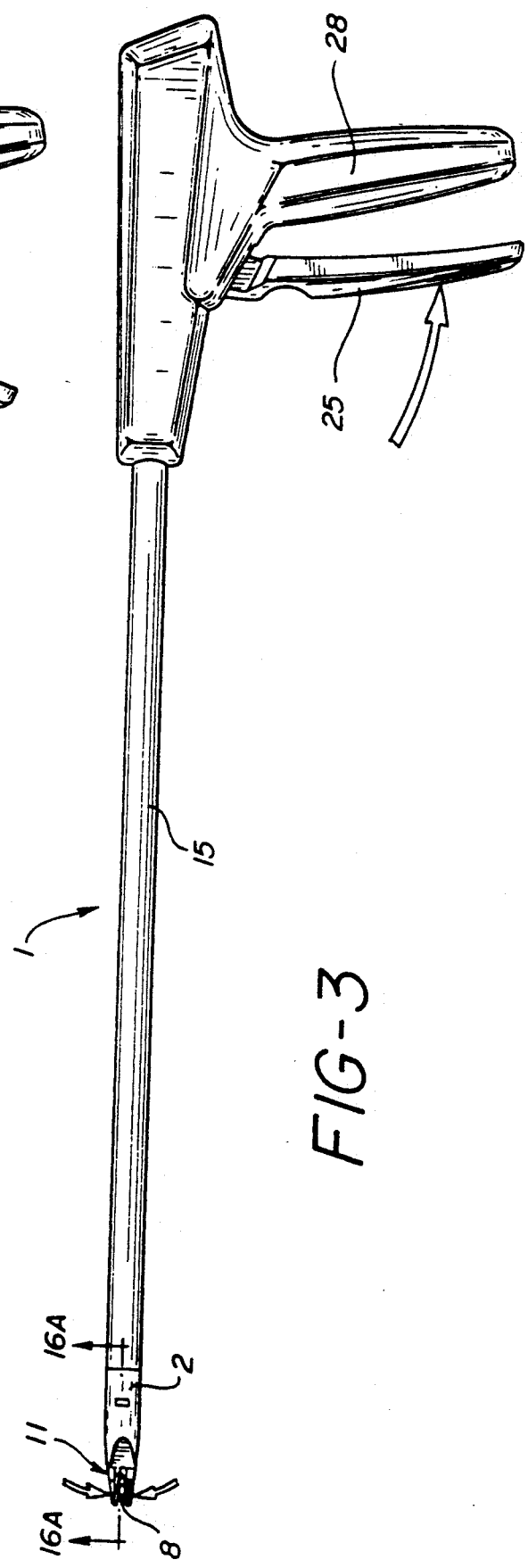

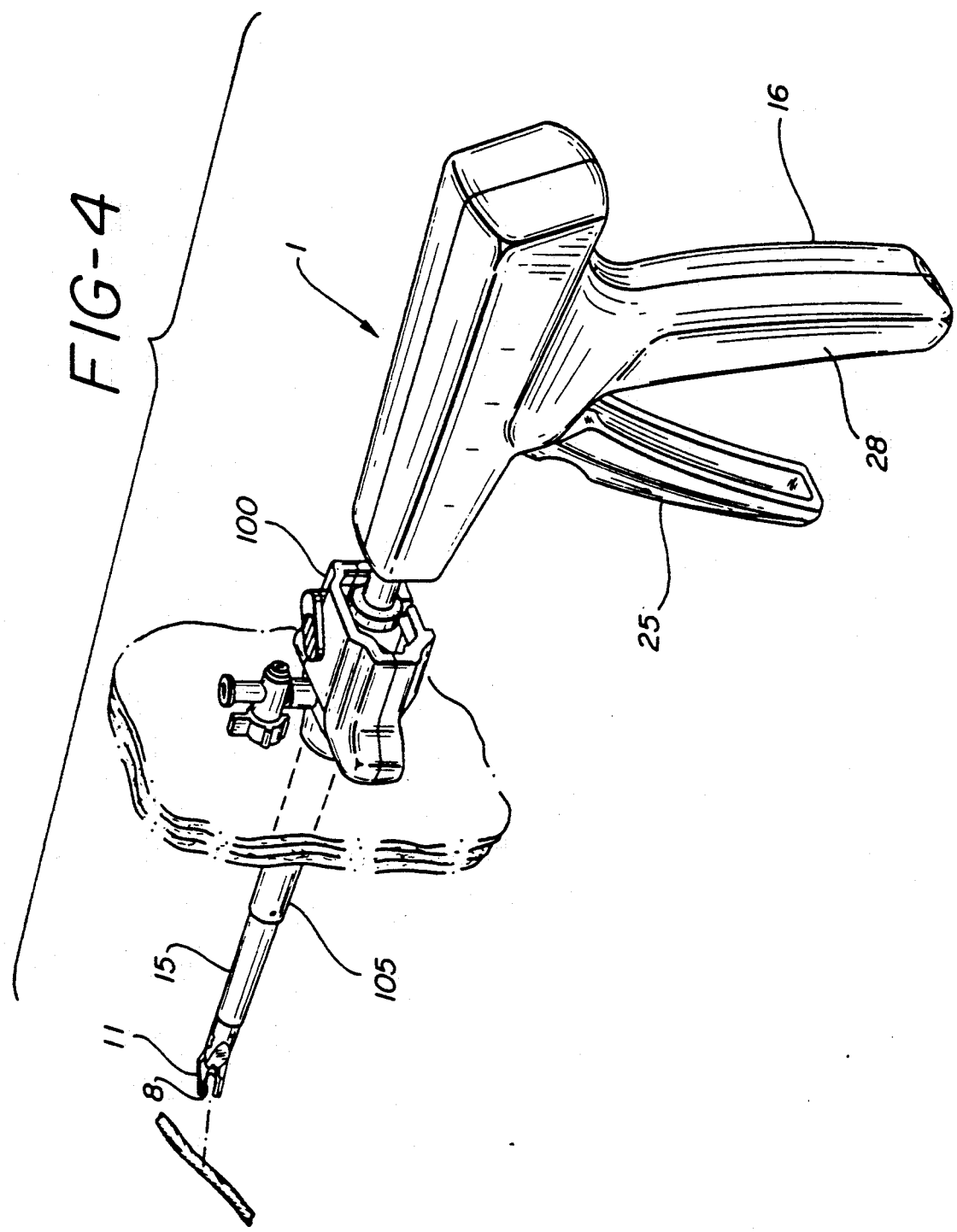

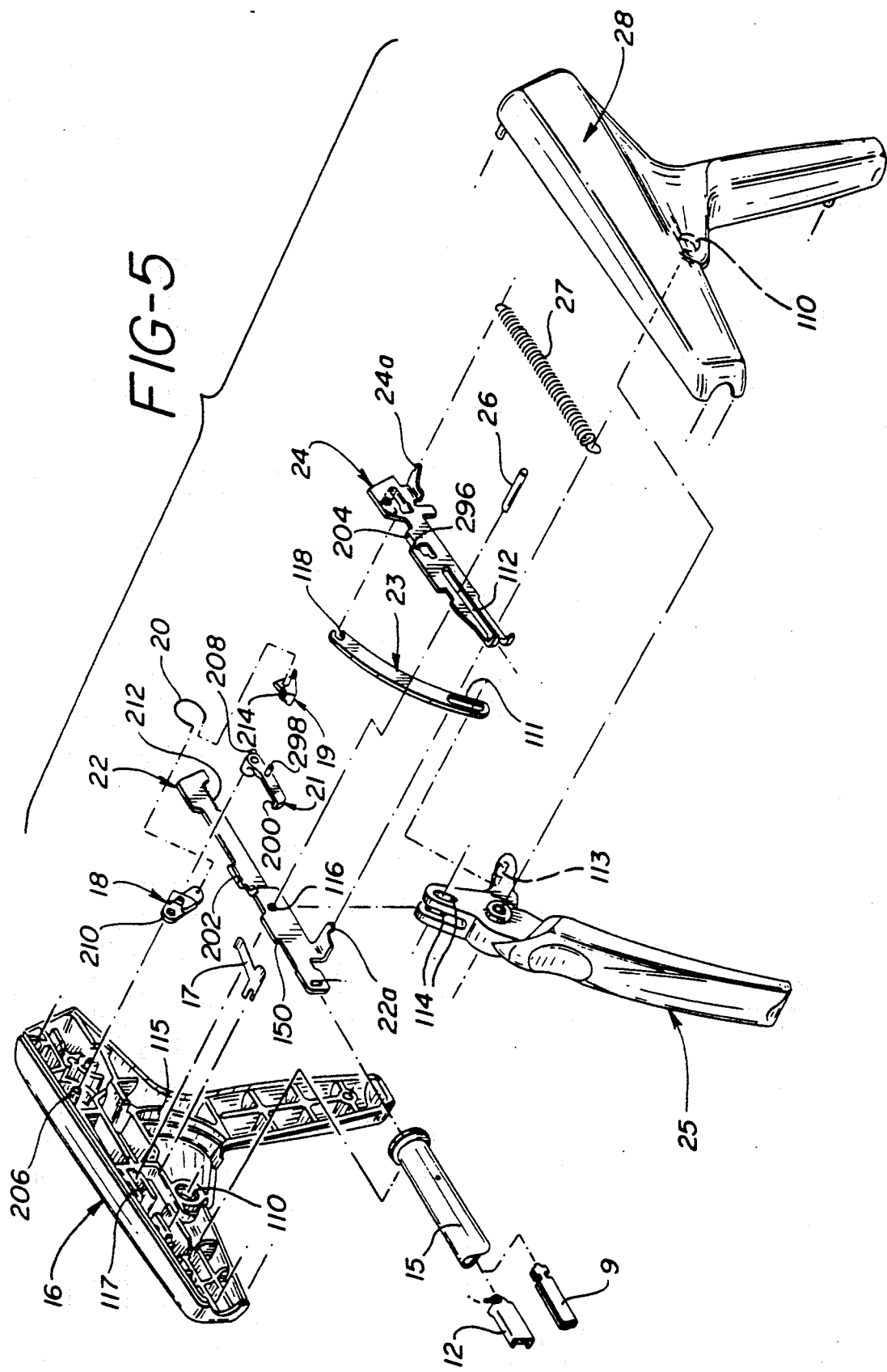

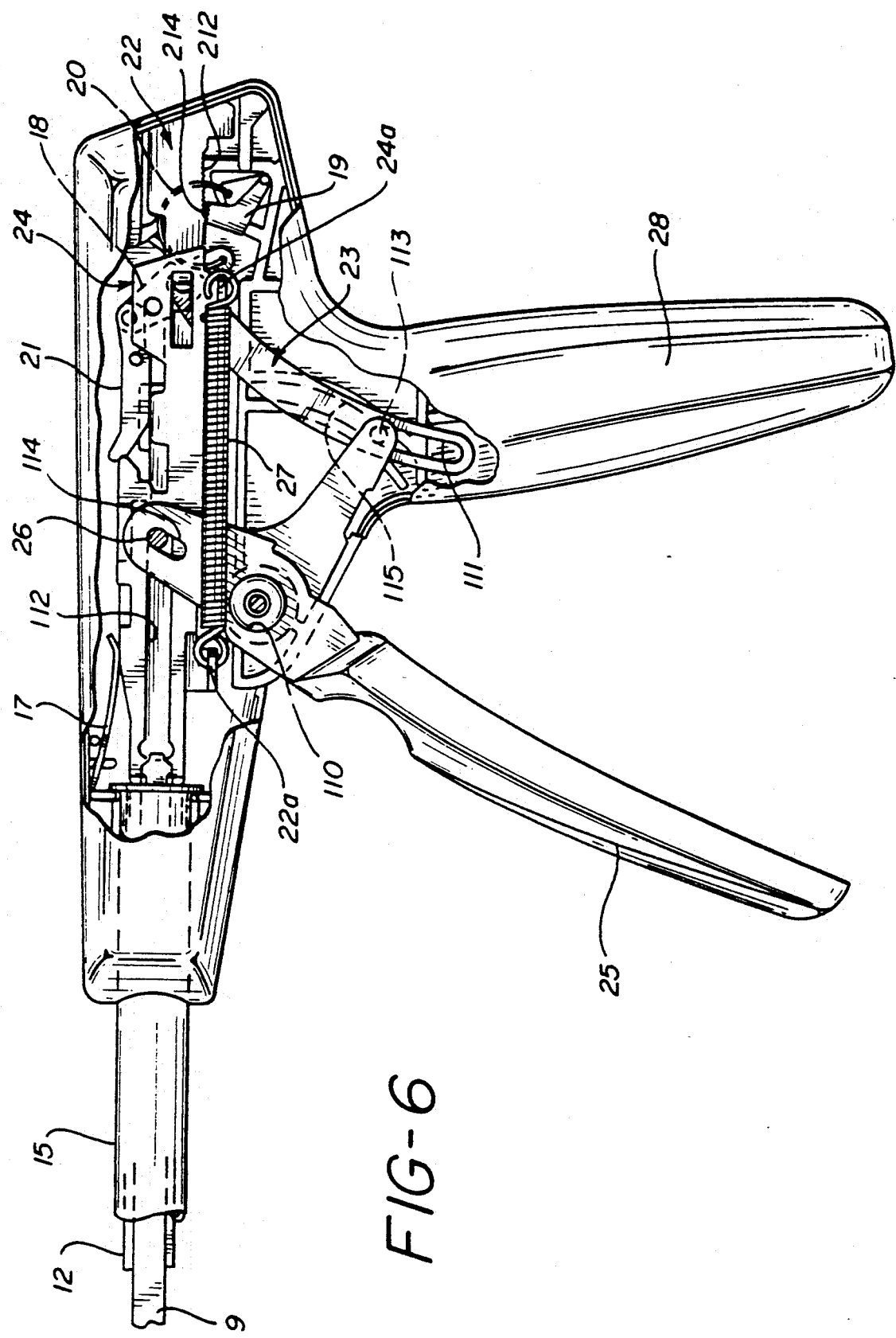

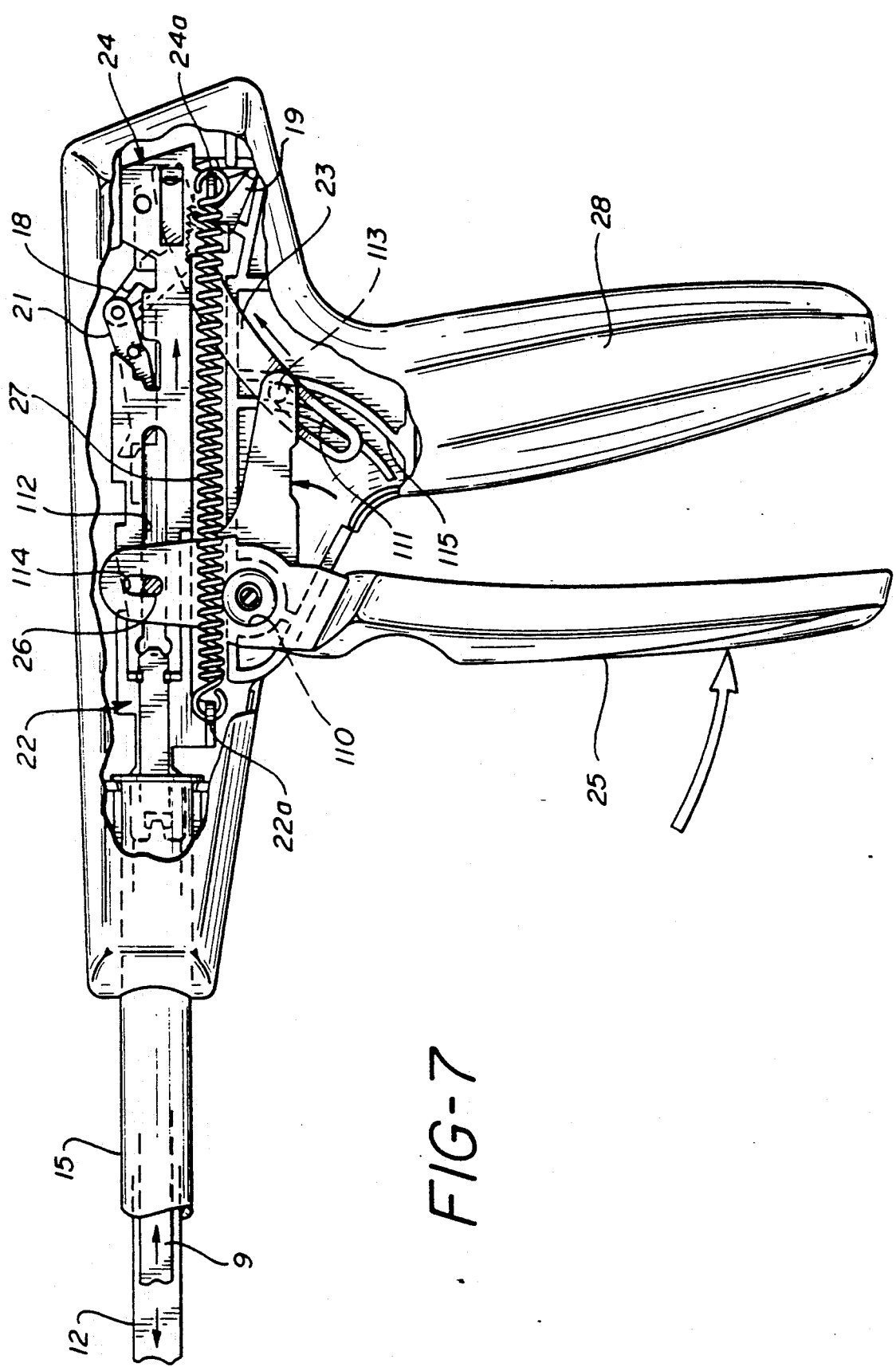

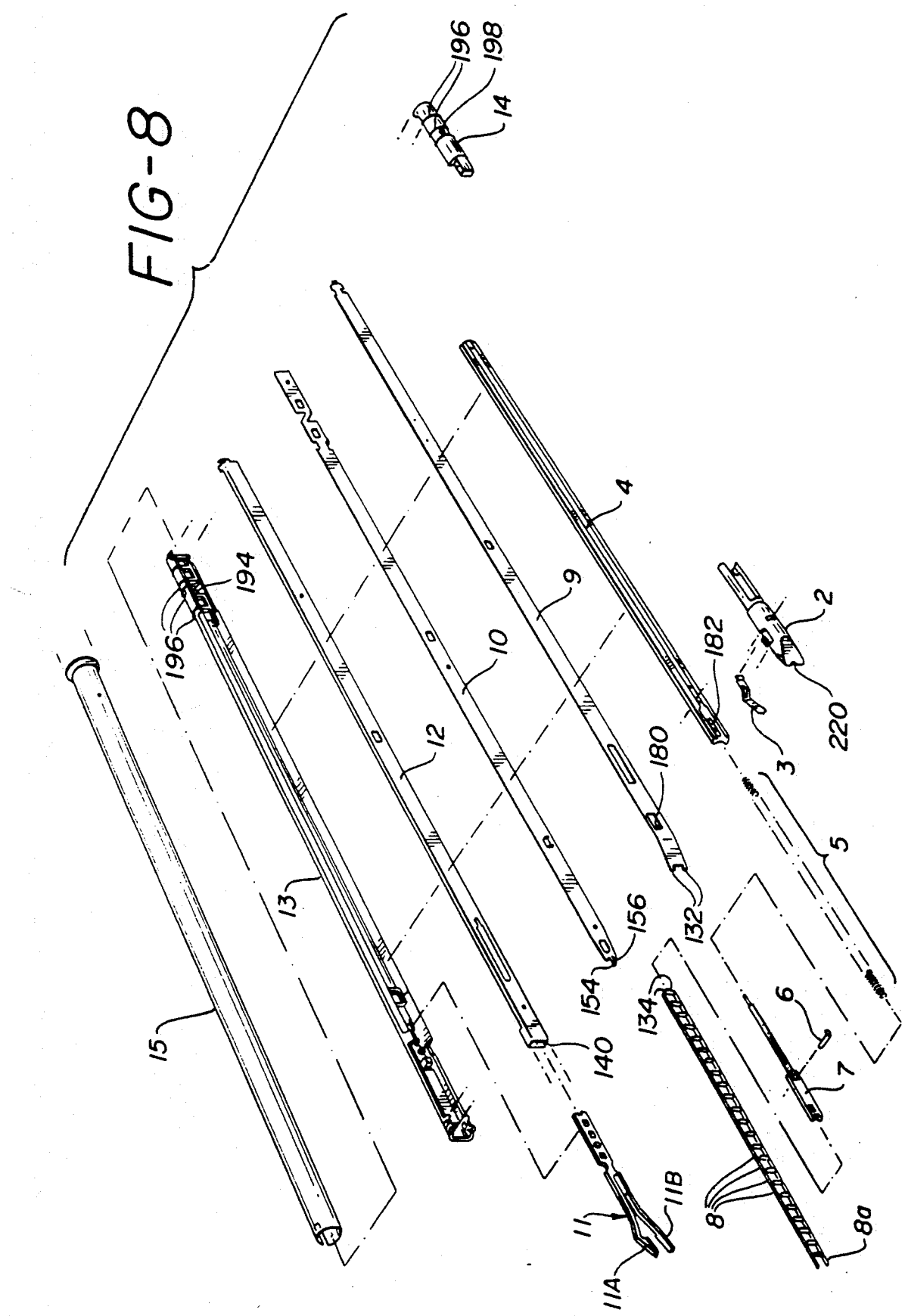

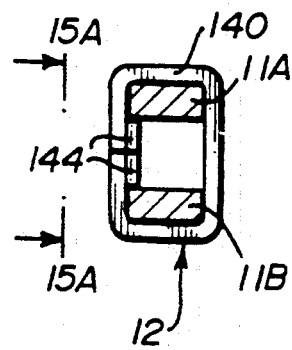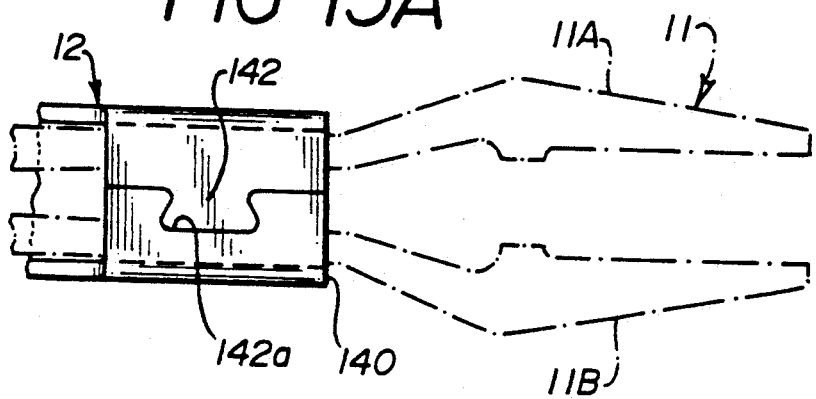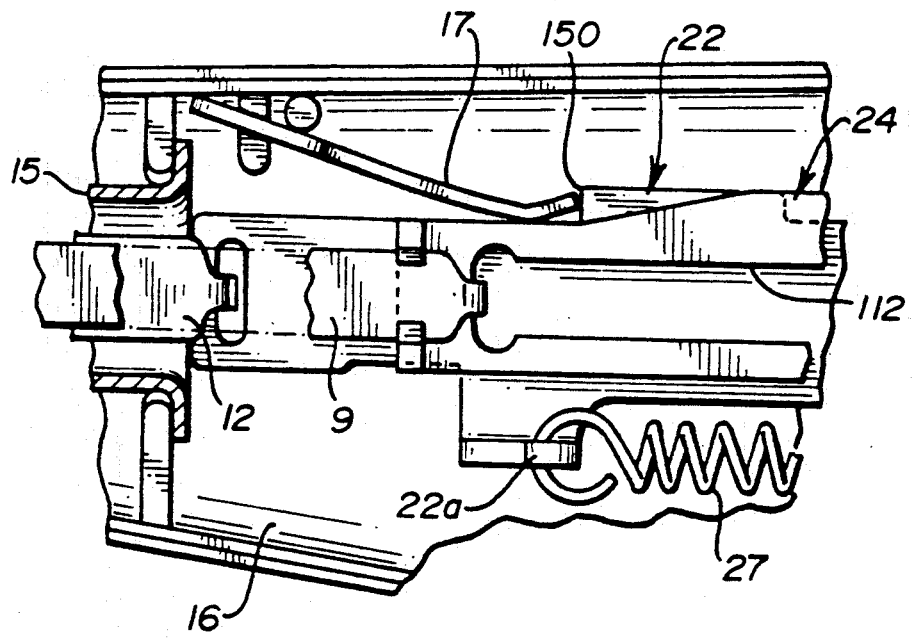

TORQUING DIRECTIONS OF ARMS

APPLICATION FORCE

TORQUING DIRECTION

ENDOSCOPIC MULTIPLE LIGATING CLIP APPLIER

FIELD OF THE INVENTION

Generally, this invention relates to ligating clip appliers. More specifically, this invention relates to endoscopic ligating clip appliers. Most specifically, this invention relates to endoscopic ligating clip appliers, where the applier is capable of placing down a sequential number of clips from a multiple clip applying cartridge.

BACKGROUND OF THE INVENTION

There have been many advances in recent years in the field of endoscopy. Many of these advances have come due to the increased versatility of endoscopic staple and clip applying mechanisms. These mechanisms are placed through the cannula of an endoscopic trocar so that tissue may be cut, stapled or ligated. With use of these endoscopic stapling and ligating mechanisms, there have become available means for the proliferation of endoscopic ligating procedures.

With the advent of these devices, however, there have been certain noted inadequacies. Many of these inadequacies have become perceived solely because of the newness of the endoscopic procedures. Thus, there has been a great opportunity for the discovery of new needs and desires of each individual surgeon, and therefore an explosion in the necessity to meet these requirements.

For instance, there has been perceived a need for venting such an endoscopic applier, in order to equalize pressures within the instrument and to provide a path of least resistance for fluid flow within the instrument. The equalization of pressures minimizes the possibility of failure of the instruments.

In addition, there has been a perceived need for adequate clip advancing mechanisms in order to both longitudinally (along the long axis of the instrument) and transversly support both the clip closing mechanism and the clip during such surgeries.

Also, there has been perceived a need for a mechanism to vary the gap of a ligating clip when closed within the mechanism.

There is yet another perceived need for a mechanism which guarantees that the jaws of the instrument are open when a clip is fed into these jaws. This mechanism insures clip presence during ligating procedures.

There is yet another perceived need for a mechanism to lockout the firing mechanism instrument after the last ligating clip in the cartridge of clips has been fired.

Yet another perceived need is for a restricting means to minimize proximal movement of the clip during application into a vessel. This limitation of movement maintains the ligating clip within the proper forming area of the jaws during ligation.

One additional need is to create a resistance to the torque acting on the endoscopic applier shaft. Resistance of such torque minimizes any transverse deflection of the endoscopic applier tip during usage. Such torque resistance promotes clip placement accuracy.

Still another perceived need is to create smaller jaw spacing, which allows the usage in a smaller cannula during endoscopic procedures. One additional problem encountered in the resolution of this problem is that one must minimize the spacing of the jaws, while still compensating for the torques created during jaw closure.

Yet another perceived need is for a system which minimizes the possibility of double feeding of clips into a clip applier jaws. Such a system may be perceived as the use of a series of valves and springs in order to properly place only one clip within the jaws of the instrument at any one time.

One additional need is for a mechanism which seals an endoscopic clip applier, to prevent the gross loss of pneumoperitoneum, during operations. Such sealing is necessary to maintain pneumoperitoneum throughout the Procedure.

One further perceived need is for a method wherein the synchronized feeding of clips into the jaws of an applier is coordinated with the opening and closing of these jaws during use.

Another final perceived need is for a mechanism which prevents backup of a clip about to be fired within such an endoscopic clip applier.

Therefore, it is to be realized that while there currently exist certain endoscopic clip appliers, it continues to be still important to improve on these appliers in many various areas where there are perceived deficiencies or inadequacies.

SUMMARY OF THE INVENTION

Accordingly, it is an object of the invention to provide an endoscopic multiple ligating clip applier with an adequate venting system to maintain the instrument from functional failure.

It is yet another object of the invention to provide a multiple ligating clip mechanism which provides for clip closure without the threat of dropping the clip from the instrument into the wound site.

It is yet another object of the invention to provide a clip closure cam channel for a multiple ligating clip instrument, so that closure of the ligating clip is improved.

It is yet another object of the invention to provide for a feature which retains the jaws in a "positive open" position, so that a clip will be fed into a pair of open jaws. This improves the reliability and performance of the mechanism.

It is yet another object of the invention to provide for a lockout mechanism which causes the instrument to be locked out once the last clip from the magazine is fired.

It is yet another object of the invention to maintain the clips firmly with the jaws during closure. This enables the user to be assured of more precisely spacing of clip legs and, resulting in an improved slip closure within the instrument.

It is yet another object of the invention to provide for a torque resisting shaft for a multiple clip applier which minimizes transverse deflection of the tip of the instrument. Such minimization promotes improved clip placement and accuracy during firing.

It is yet another object of the invention to provide within a multiple clip firing instrument, an anti-torque feature on the jaws of this device. This feature should be designed to allow the size of the jaws to be minimized, while still maintaining and providing adequate clip closure characteristics.

Yet another object of the invention is to provide for a clip feeding system which improves the clip feeding reliability by minimizing the possibility of double feeding of the clips into the jaws.

It is yet another object of the invention to provide for a sealing system within the endoscopic multiple clip applier so that it maintains pneumoperitoneum throughout use of the system.

One other object of the invention is to provide a timing mechanism for an endoscopic multiple clip applier wherein it is assured that a clip is fed from a clip stack into the jaws of the mechanism during the time between when the jaws are spaced apart so as to be able to accept such a clip, and yet before the instrument has been fully released to its open or "ready to fire" position.

It is yet another object of the invention to provide for a tissue stop which prevents tissues or vessels held within the clip applier from being improperly positioned on the instrument. Such a mechanism is advantageous in order to promote secure clip closure and placement within the context of a multiple fire ligating clip mechanism.

These and other objects of the invention are provided for in an endoscopic ligating clip device which contains a firing mechanism held remotely from an endoscopic clip applying portion by a long solid cannula. The device is created so that the clips are applied in one orientation, but it is understood that the clip applier can be rotated to advantageously orient the system. Within the clip applying mechanism there is described a venting system which comprises a channel through which the device may be vented. This helps insure adequate firing within the system. There is also described a feed bar support mechanism which contains a pair of protrusions which prevent the deflection of the clip applier jaws during its insertion into the cannula. Furthermore, there is described a cam channel mechanism which provides a uniform closing force upon the ligating clip held within the jaws. A tab within the cam channel prevents the jaws from closing, so that these jaws may assurably receive a new clip after the instrument has been fired to place a clip around tissue.

Other novel features are provided in this system. First, there is a mechanism comprising a lever which falls into the firing path of the device so that the instrument cannot be fired after the last clip has been fired from the mechanism. Second, a finger located on the clip applying mechanism is described, which securedly holds the clip about to be fired in place on the jaws of the instrument. Third a torque-resisting shaft is placed on the instrument, to prevent transverse deflection of the tip of the instrument during firing.

Another unique feature of the instrument is located in the jaws, which provide multiple contact points during firing, minimizing deflection in the arms of the jaws, enabling proper closure of the clip. This minimization of deflection provides for more consistent and improved clip closure. A clip feeding escapement system provides that only one clip is actually inserted within the open jaws after the previous clip has been fired. Furthermore, there is a sealing system provided for in the mechanism which adequately provides the sealing of pneumoperitoneum. Also, there is located on the shroud of the instrument a v-shaped notch, which helps maintain the tissue on the jaws of the instrument. This notch helps secure proper position of the tissue for firing of the instrument and clip closure.

This device has been described in connection with a number of various features contained in its embodiment. These features will be better understood when taken in connection with the attached Detailed Description of the Drawings and described in connection with the following Detailed Description of the Invention.

DESCRIPTION OF THE DRAWINGS

FIG. 1 is a perspective view of the left hand side of the endoscopic multiple clip applying instrument of this invention;

FIG. 2 is a side plan view of the instrument of the invention in the open position;

FIG. 3 is a side plan view of the instrument of the invention in the closed position;

FIG. 4 is a perspective view of the instrument of the invention inserted through a trocar;

FIG. 5 is an assembly view of the handle of the invention;

FIG. 6 is a partial cut-away view of the handle of the invention in its relaxed position;

FIG. 7 is a partial cut-away view of the handle of the invention in its firing position;

FIG. 8 is an assembly view of the tubular endoscopic portion of the instrument of the invention;

FIG. 15 is a cross-sectional view of the invention describing the cam channel mechanism taken across lines 15—15 of FIG. 2;

FIG. 15A is a cross-section view taken across lines 15A—15A of FIG. 15;

FIG. 16 is a cross-sectional view of the invention describing the handle-latch combination;

DETAILED DESCRIPTION OF THE INVENTION

Figure 9:
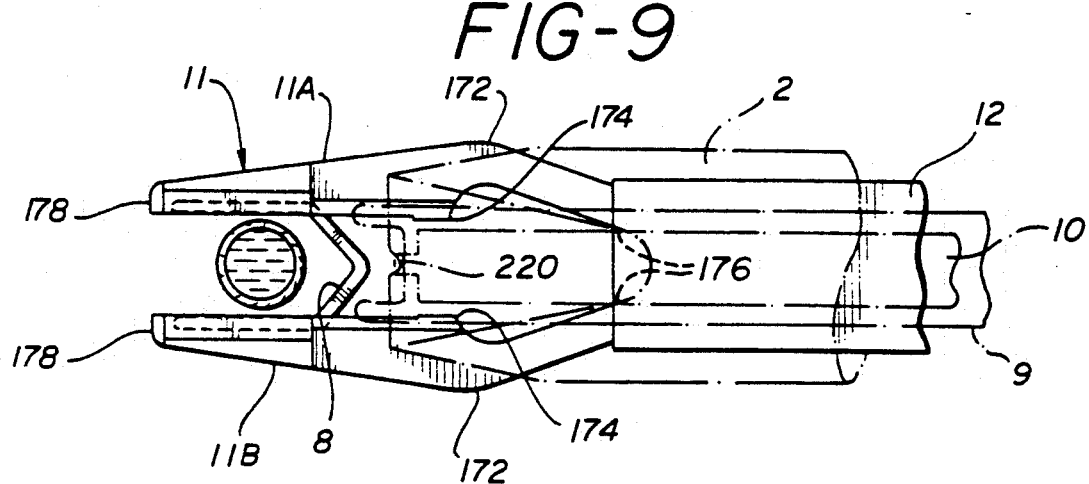
FIGS. 9, 10 and 11 are sequential plan views of the clip as placed in the jaws of the invention when in the open, closing and closed positions respectively.

An endoscopic multiple ligating clip application mechanism 1 can be seen in FIGS. 1-22. As better seen in FIGS. 1, 2, 3 and 4, this multiple ligating clip mechanism 1 is useful for applying clips through a surgical trocar 100. As seen in FIG. 4, the ligating clip mechanism 1 is applied through the cannula 105 of a trocar 100, so that a vessel can be occluded or tissue can be clamped. The mechanism applies the forwards nest clip 8 a series of clips by means of jaws 11 which are fired remotely by a trigger 25. As seen in FIGS. 2 and 3, the trigger 25 is compressed, causing the jaws 11 to close, and squeezing a ligating, clip 8 therein. After closing the forwardmost clip 8, the jaws 11 are released and there is loaded another clip 8 in its place. As used herein, jaws 11 containing jaw arms 11a, 11b, will be used interchangeably.

As better seen in FIGS. 5, 6 and 7, there is described handle halves 16, 28 which contain the trigger 25 mechanism for firing the device. The handle halves 16, 28, surround the firing mechanism and afford a pivot point 110 around which trigger 25 rotates. Trigger 25 is associated with a former plate 22 and a feeder link 23. As seen on the right hand side of FIG. 5, feeder link 23 is attached to the trigger 25 in that pivot 113 fits in slot 111. Further, feeder link 23 abuts feeder plate 24 to hold it positionally within handle halves 16, 28. Feeder plate 24 is connected to return spring 27. Feeder plate 24 contains post 24a which is in turn connected to a post 22a on former plate 22. Thus, when the trigger is fired, the former plate 22 is pushed forward. Pivot 113 on trigger 25 slides in channel 115 in handle half 16 and causes slot 111 to be urged toward the rear of the instrument. Slot 118 on feeder link 23, in turn, causes feeder plate 24 to be urged to the rear of the instrument. Simultaneously trigger 25 rotates so that slots 114 causes dowel pin 26 to slide in slot 112 of plate 24. Also, dowel pin 26 urges point 116 in former plate 22 forward, as it slides within slot 117 in handle half 16. When the trigger 25 is released, the tension on return spring 27 causes the trigger 25 to return to its original position. This motion causes feeder plate 24 (through post 24a) and former plate 22 (through post 22a) to be similarly effected, so that rigger 25, dowel pin 26, and former plate 22 are returned to their non-stressed positions. Dowel pin 26 maintains feeder plate 24 so that it is assumes a place on right handle half 16. An anti back-up lever 19, lost motion lever 18, latch 17, and torsion spring 20 and precock trigger 21 will all be further described as part of this invention.

When the trigger 25 is activated, the former plate 22 is caused to move forward so that cam channel 12 connected to former plate 22 within support tube 15 is moved forward. This actuates the endoscopic clip applying mechanism. As seen in FIG. 8, the feed bar 9 and cam channel 12 surround floor 10. These mechanisms are sealed between lower, shroud 13, and seal cap 14 within the support tube 15. Inserted within cam channel 12 is jaw 11. This jaw will close about a ligating clip 8 to seal tissue or vessels.

Held between support tube 15 and clip track 4 are feeder spring 5, lock lever 6, feed shoe 7, and a series of clips 8. The clip track 4 is capable of advancing forward a series of clips and loading them within the arms of jaw 11. A lifter spring 3 is held in place over clip track 4 by top shroud 2, and will place the first clip 8a of a stack of clips 8 into the plane of feed bar 9 to be positioned into jaws 11. Also, the seal cap 14 and lower shroud 13 hold cam channel 12, floor 10 and feed bar 9 in place within the support tube 15.

In operation, the trigger 25 is fired and former plate 22 causes cam channel 12 to move forward. Cam channel 12 encloses jaws 11 to seal a clip 8 around tissue. After trigger 25 is released, cam channel 12 retracts so that jaws 11 open. The magazine of clips 8 is advanced forward so that another clip 8 is held within jaws 11. This occurs when spring 27 is released, causing feeder plate 24 to advance. This in turn causes feed bar 9 to advance the first clip 8a from the stack of clips 8 which has been positioned in the path of the feed bar 9 by spring 3 into jaws 11. This operation can best be seen by observing FIGS. 9, 10 and 11 in conjunction with FIGS. 6 and 7. Of course, each of the mechanisms as disclosed by this invention will be further described herein.

Specifically, it is to be noted that the orientation of clips 8 is transverse to that of the orientation of the handle portion of the instrument 1. In this way, the user is able to grip the trigger 25 on the handles 16, 28 of the instrument 1 so that the user's hand is held parallel to the plane on which the clips are fired. This affords a more typical reference point for the user, so that it is more comfortable for operation of the instrument.

Figure 12:
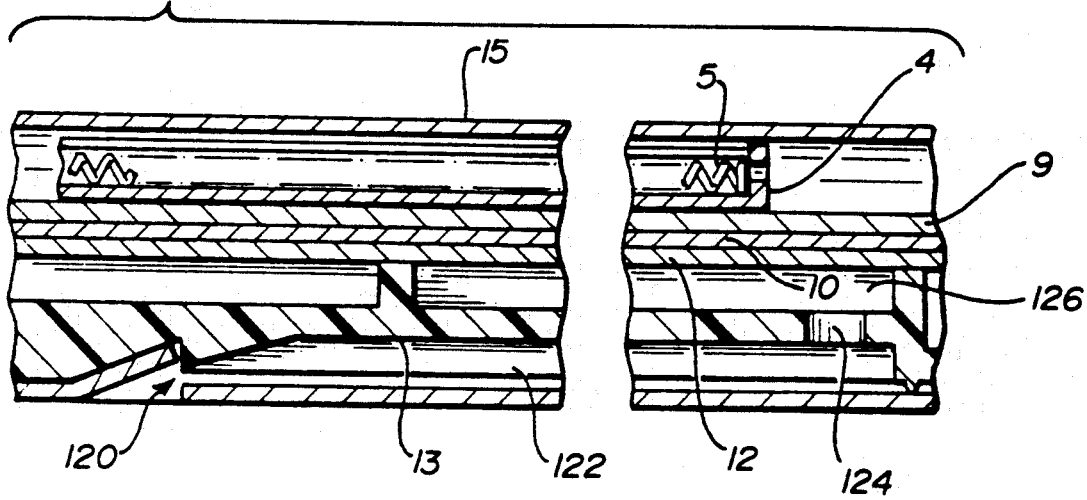
FIG. 12 is a longitudinal cross-sectional view of the invention taken across lines 12—12 as seen in FIG. 2.

Now, each of the various features of the clip applying mechanism will be described. The first feature is a venting system for endoscopically applying these clips. As seen in FIG. 12, there is located a vent 120 on the outside of the instrument. This vent 120 is attached to an open channel 122 within the lower shroud 13 within the support tube 15.

Open channel 122 is connected to a hole 124 in the lower shroud 13. This allows fluid passage between tube 15 and lower shroud 13. This hole in lower shroud 13 affords fluid passage between the upper portion 126 of the instrument and the inner channel within lower shroud 13. This open channel 122 within support tube 15 runs along the longitudinal axis of the support tube 15 and provides a path of least resistance for fluid flow between the abdominal cavity and the inside of the instrument 1, such that pressure is capable of being equalized in the instrument. The hole 124 in the lower shroud 13 at the end of this channel 122 provides a venting path to the upper portion 126 of the shaft assembly. Fluid held at higher pressures before insertion, is therefore vented from the instrument 1. The instrument is much more capable of functioning under between 10 and 15 mm mercury pressure. Pressure is equalized across the entire instrument, and a path of least resistance is provided. In this way, the likelihood of functional failures of the instrument when used operatively is reduced.

Figure 13:
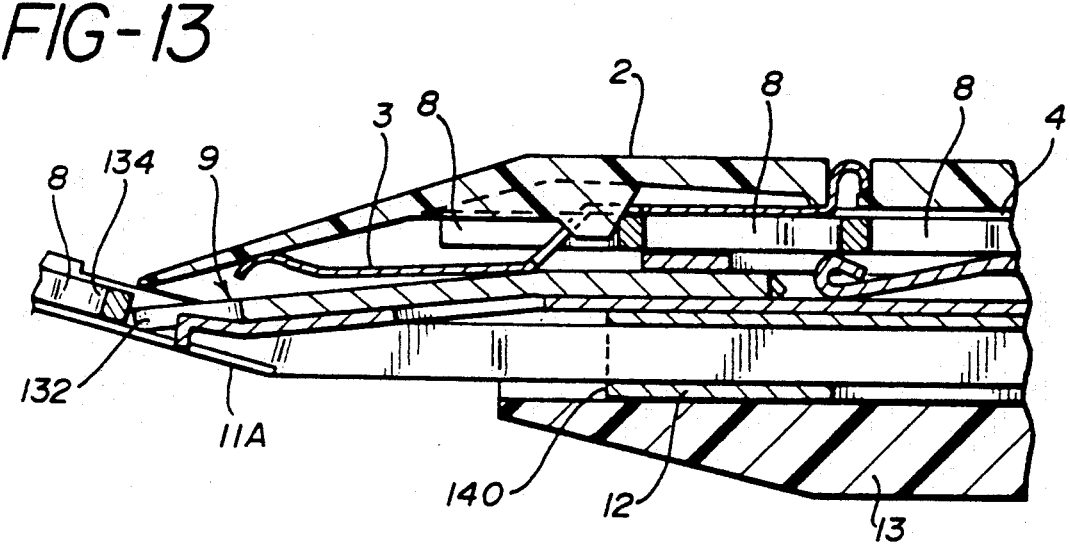
FIG. 13 is a cross-sectional view of the invention taken along lines 13—13 as seen in FIG. 1.
Figure 14:
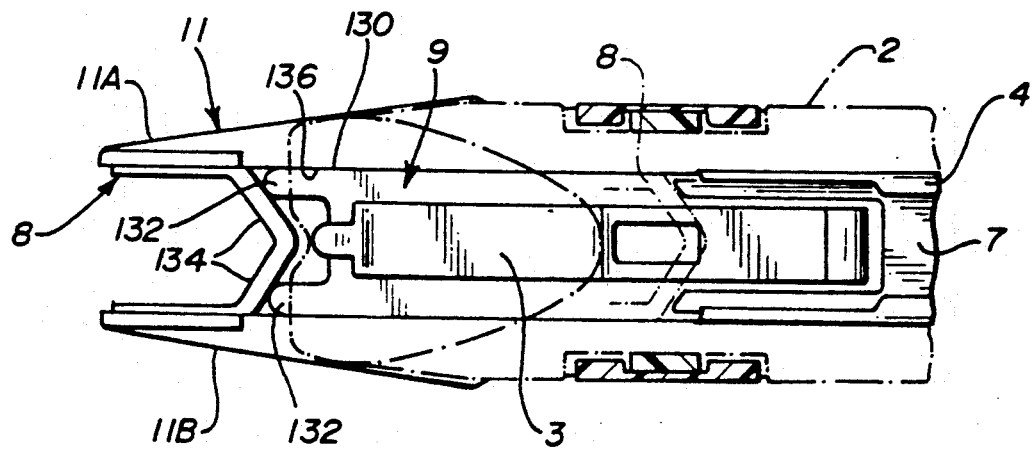
FIG. 14 is a cross-sectional view as taken across lines 14—14 of FIG. 1.

Furthermore, as seen in FIGS. 13 and 14, there is also disclosed a reinforcement or support mechanism for the endoscopic multiple clip applier. This support mechanism provides longitudinal reinforcement or support for the ligating clip 8 during application onto tissue, and transverse support of the jaws 11 during insertion through the cannula 105 of the trocar during endoscopic surgery. This reinforcement scheme provides for a more reliable system. As seen in FIGS. 13 and 14, when the instrument jaws 11 are opened the ligating clip 8 is positioned between the jaws 11a, 11b of the instrument. The feed bar 9 is advanced completely forward. When the instrument is inserted through a cannula of a trocar and applied to tissue it is important that the jaws are prevented from closing. As seen in FIG. 14, there are outboard protrusions 132 on the feed bar 9. These outward protrusions 132 contact the angled arms 134 of the clip 8 in the jaws. Also, the feed bar 9 has a tapered outer edges 130 which contacts the inner edges 136 of the jaw 11.

Thus, jaws 11a, 11b are prevented from being squeezed transversely during insertion through a cannula 105. The outboard protrusions 132 prevent the clip 8 from moving longitudinally during insertion, and the outer edges 130 of the feed bar 9 prevent the inadvertent jaw closure during insertion. This aspect advantageously promotes improved clip closure and prevents dropping of a clip from the instrument into the wound site during usage.

Another feature is the clip closure cam channel 12 used in this instrument. Cam channel 12 helps close the jaws 11 of the ligating clip instrument. The cam channel mechanism 12 travels longitudinally along the axis of the tubular support tube 15 of the instrument. The cam channel 12 lies in the longitudinal axis of the jaws 11. The distal end 140 of the cam mechanism is rectangular and cross sectioned, as can be seen in FIG. 15. As in FIG. 15A, on the anterior surface of the cam channel 12 there is a dovetail joint 142, 142a, which holds the cam channel 12 together mechanically. This dovetail mechanical lock reduces the transverse (side-to-side) deflection of the cam channel 12 during clip formation. In this way, while the longitudinal motion of the cam channel 12 takes place, transverse motion of the cam channel 12 is prevented. Therefore, the dovetail mechanical lock 142, 142A incorporated into the cam channel 12 improves the dimensional stability cam channel 12 and improves the reliability of closure of the ligating clip 8.

As also seen in FIG. 15, there is described a pair of tabs 144 in the cam channel 12. These tabs 144 are bent at the distal end of the cam channel 12 and are oriented perpendicularly through the longitudinal axis of the jaws 11 containing containment arms 11A, 11B of the instrument 1. When arms 11a, 11b are open, the outer edges of the tabs 144 rest on the arms of 11A, 11B of the jaws 11, preventing them from being moved inwardly toward each other, as during closure of the mechanism. It will be noticed that the profile of jaws 11a, 11b is the same thickness as shroud 15, thus enabling a clip to be loaded within the jaws and then inserted through a trocar cannula, as seen in FIGS. 2 and 15. When there is a ligating clip 8 closed within the jaws 11, the cam channel 12 retracts from the forming site and the edges of the tabs 144 again contact the edges of the jaws 11, forcing the jaws 11 outward. This guarantees that the jaws are open to receive a clip. Clip feeding reliability of the instrument is increased, while not compromising the process of clip closure.

Figure 16A:
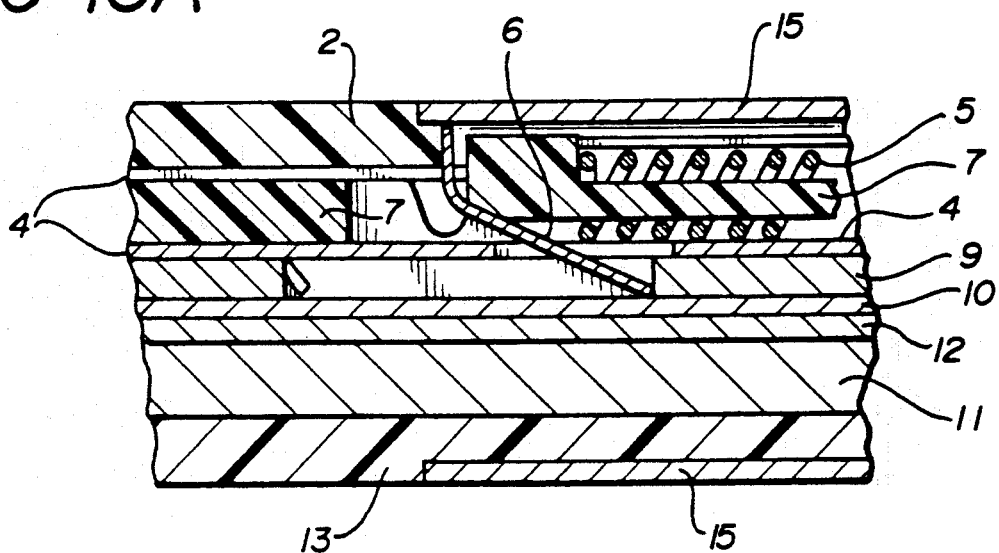
FIG. 16A is a cross-sectional view of the invention taken across lines 16—16 of FIG. 3 emphasizing the lockout mechanism used in the endoscopic clip applier.

As seen in FIG. 16A, there is also described in this instrument a pivoting lock-out lever 6, which is attached to the feeder shoe 7. The lever 6 pivots upon contact with top shroud 2 into the path of the feed bar 9, as seen in FIG. 16A. This lever 6 when downwardly pivoted, as seen in FIG. 16a, prohibits the complete forward motion of the feed bar 9. This then causes the biased latch 17 to engage wall 150 of the former plate 22, seen in FIG. 16. Therefore, this multiple redundant system allows for locking of the instrument after the last clip 8 is fired at the forward end of the instrument by the jaws 11 (by biased latch 17), as well as at the rearward end of the instrument (by lever 16). The lock-out lever 6 pivots into place only when there are no remaining clips 8 in clip track 4. Had there been a remaining clip 8, the feeder spring 5 would not have been able to bias feed shoe 7 to clear the path for the lock-out lever 6, such that lever 6 is caused to pivot into the path of the feed bar 9. When this locking out by lever 6 occurs, the feed bar is prevented from completely moving forward and therefore the biased latch 17 engages the wall 150 of the former plate 22.

Figure 16B:
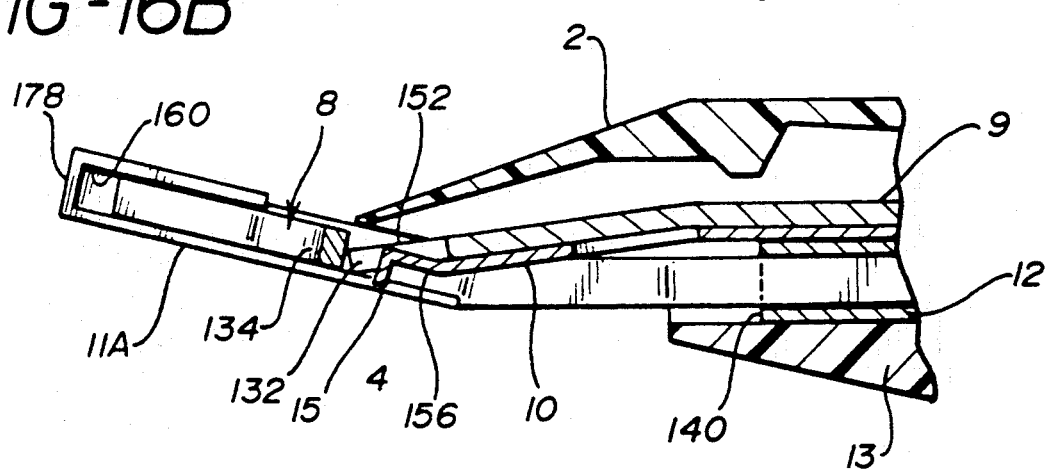
FIG. 16B is a cross-sectional view of the invention taken across lines 16—16 of FIG. 3, emphasizing the rearward retention mechanism for the clip applier in the open-state with an unformed clip of the invention.
Figure 16C:
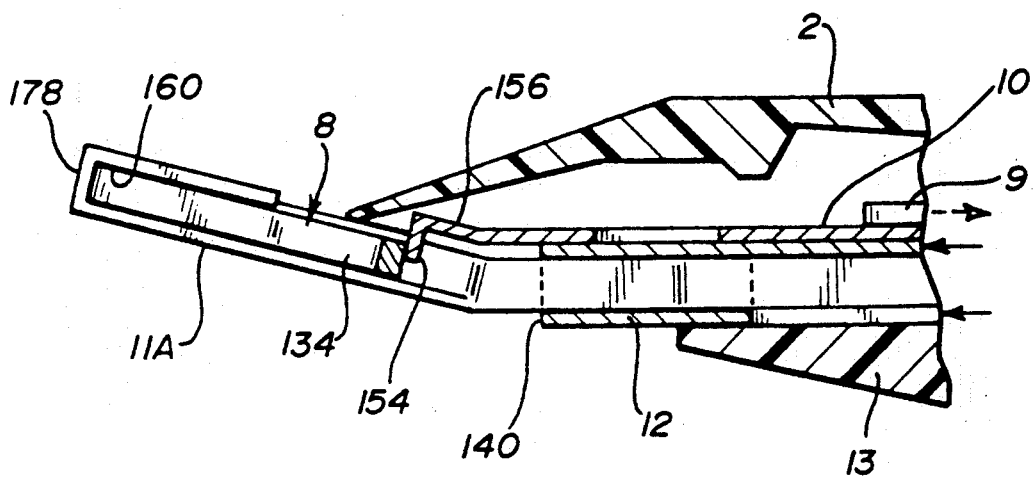
FIG. 16C is an identical view as FIG. 16B, except that it demonstrates the jaws in a closed state, with a formed clip.

Also, as seen in FIG. 16B, there is described a mechanism that minimizes the rearward movement of a clip 8 in the applier during application onto the vessel. It is also capable of maintaining the clip 8 in its proper forming area throughout complete closure of the mechanism. This mechanism comprises the floor 10 held within support tube 15. The floor 10 protrudes into the longitudinal plane of the clip forming area 160 of the jaws 11A, 11B of the instrument. A clip retaining finger 156 on the floor 10 is provided with a perpendicularly bent tab 154 at its distal end, as seen in FIG. 16B. This retaining finger is unitary to the floor 10 and is also biased so that it is parallel with the longitudinal plane of the jaw clip forming area 160. Initially, a clip 8 is held in place by end 152 of feed bar 9. Distal tab 154 of the finger 156 is positioned perpendicularly to the forming area such that the tab minimizes the rearward movement of the clip 8 within the jaws 11A, 11B. As the jaws close, the floor 10 is ramped out of the plane of the clip forming area. Yet, throughout closure of the clip and ramping of the floor 10, the bent tab 156 of the clip retaining finger remains in the plane of the clip 8 and clip forming area 160 of the jaws 11A, 11B and is positioned behind the apex of the clip 8. This is better seen in FIG. 16C. Therefore, the movement of the clip 8 as held within the jaws 11 is always controlled and the finger 156 and tab 154 of the floor 10 constantly remain in the plane of the forming of a clip 8.

As may be seen in FIG. 8, support tube 15 is torque resistant. That is, the support tube 15 is cylindrical and hollow and is made of a non-resilient material. The tube ends near the distal end of the instrument and close to the clip forming jaws 11. Support tube 15 connected to the top shroud 2. The combination of these elements provides the necessary resistive against lateral motion of jaws 11 to allow the mechanism to properly form a clip 8. Because the material from which the support tube 15 is made is nonresilient, the stability of the instrument is increased and this helps increase the placement accuracy of a clip 8.

The jaw member 11 includes a pair of spaced apart arms 170 that define jaws 11A, 11B. The jaws 11A, 11B have a distal end portion and a proximal end portion. The distal end portions include clip receiving channels for receipt of a surgical clip therein. The channels include an end wall at the distal ends 178 thereof to close the clip receiving channels. The distal and proximal end portions have outer surfaces. The outer surface of the proximal end portion defines a ramp or cam surface 172.

Figure 17:
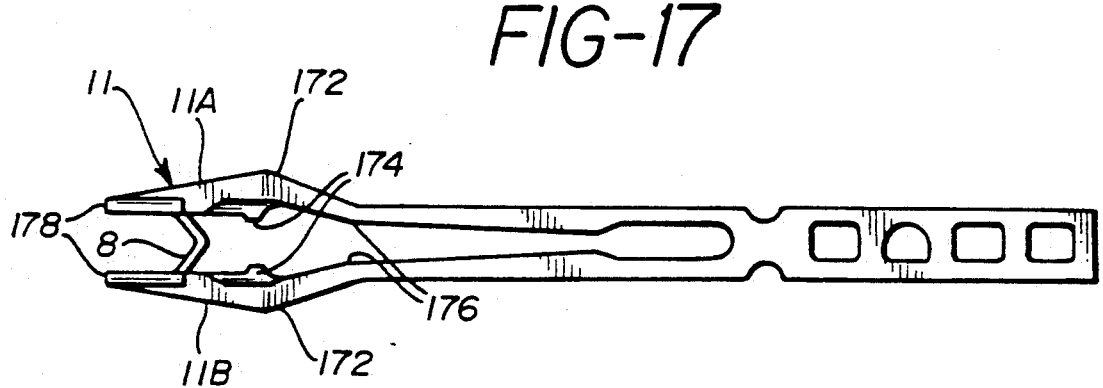
FIG. 17 is a plan view of the jaw component of the invention.

As seen in FIGS. 17, 18, 18A and 18B, the jaws 11A, 11B of the instrument are described so that they contact at their distal end 178 and at primary heel 176 located proximally to the closing ramps 172 of each jaw. This is better seen in 18 and 18A. As seen in FIG. 17, the jaws 11A, 11B are generally maintained in an open position. The contact of the primary heels 176 minimizes the lateral deflection in the arms 170 of the jaws 11A, 11B with respect to support tube 15, to properly close a clip 8. This initial contact minimizes arm deflection and torque and supports the system during loading.

Figure 18:
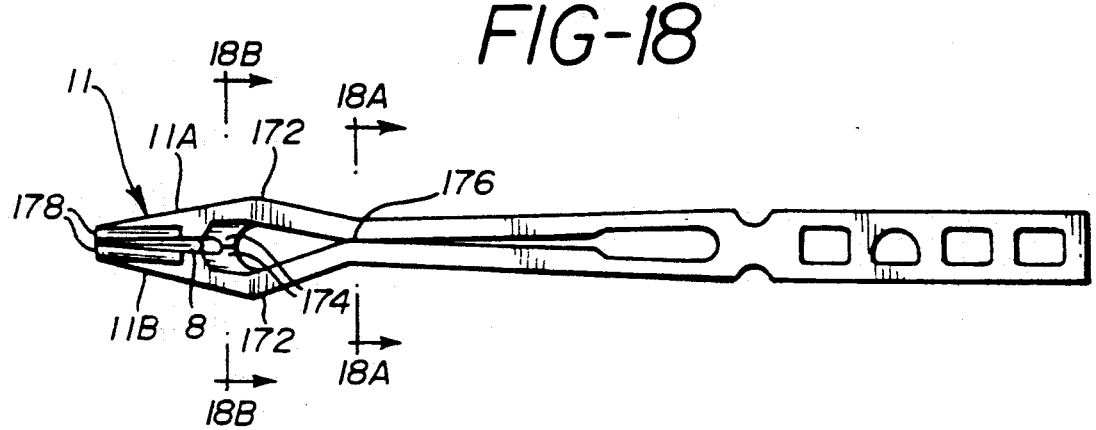
FIG. 18 is a view of the jaw as seen in FIG. 17 when in the closed position.
Figure 18A:
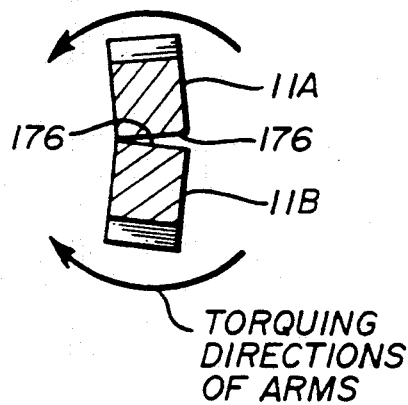
FIG. 18A is a cross-sectional view across lines 18A—18A of FIG. 18.
Figure 18B:
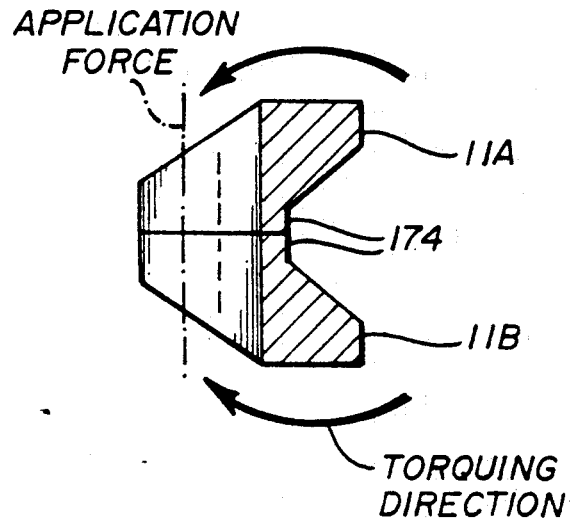
FIG. 18B is a cross-sectional view across lines 18B—18B of FIG. 18.

When the jaw is fully closed, as seen in FIGS. 18 and 18B, the last portion of clip closure causes the magnitude of loading conditions to increase. Two opposing posts positioned on the ends of clip retaining arms 170 of jaws 11A, 11B, 174, called anti-torque posts, contact with each other near the forming areas of the jaws and counteract the torque placed on the jaws. This provides for a more consistent and improved clip closure. Also, the tips 178 of each jaw contact. Thus, with the anti-torque mechanism described herein, the jaws may be smaller in size as they do not need to be as torque resistant. The jaws 11A, 11B also provide improved clip closure mechanism because deflection is minimized. This provides for reliability of the instrument along with minimization of size.

Figure 19A:
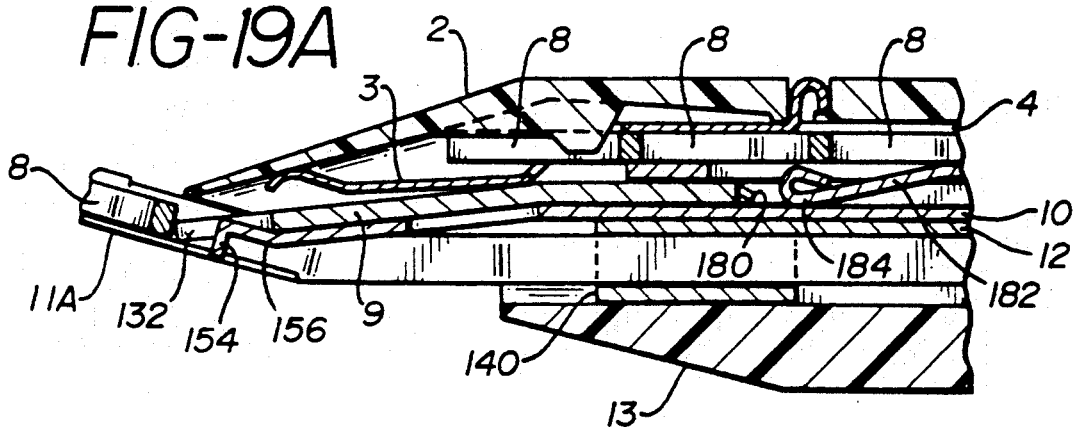
FIG. 19A is a cross-sectional view of the clip feeding escapement system of this invention across lines 19A—19A of FIG. 1.
Figure 19B:
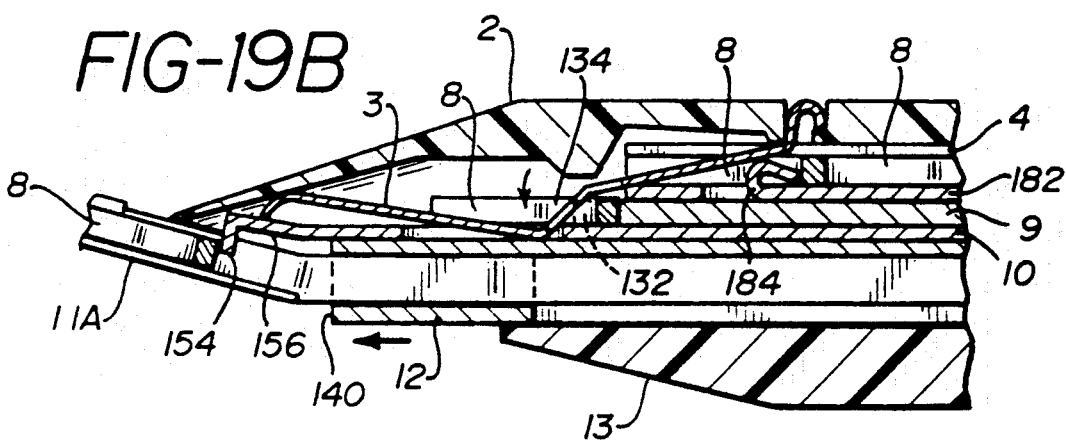
FIG. 19B is the view of FIG. 19A in the closed position.

As seen in FIGS. 19A and 19B, there is described a feeding and escapement system which improves the clip feeding reliability of the endoscopic multiple clip applier 1. This is done by minimizing the possibility of double feeding of clips into the jaws. The system consists of two independent parts. A valve 182 unitary to the clip track 4 holds the stack of clips 8 stationary while the forwardmost clip 8 is biased by lifter spring 3 into the plane of feed bar 9 (Clip 8" is positioned between jaws 11a, 11b for closure). As the instrument is actuated, the feed bar 9 is caused to retract toward the rear of the instrument, and from the lifter spring 3. When the feed bar 9 retracts, the ramp 180 on feed bar 9 is engaged with primary valve 182 located in the clip track 4, thus, clip track 4 is closed.

When clip track 4 is closed, the stack of clips 8 is held stationary. As the feed bar 9 retracts further from lifter spring 3, valve 182 is closed by ramp 180, and lifter spring 3 is actuated, causing the forward most clip 8' to be biased into the plane of the feed bar 9 so that it may be the next clip 8 loaded within the jaw. This is better seen in FIG. 19B. Only one clip 8', however, can be biased toward the feed bar, because the primary valve 182 located in clip track 4 previously uses check port 184 to hold back any additional clips 8 in the clip stack. The possibility of double feeding of clips is reduced, improving the reliability of the applier.

Figure 20:
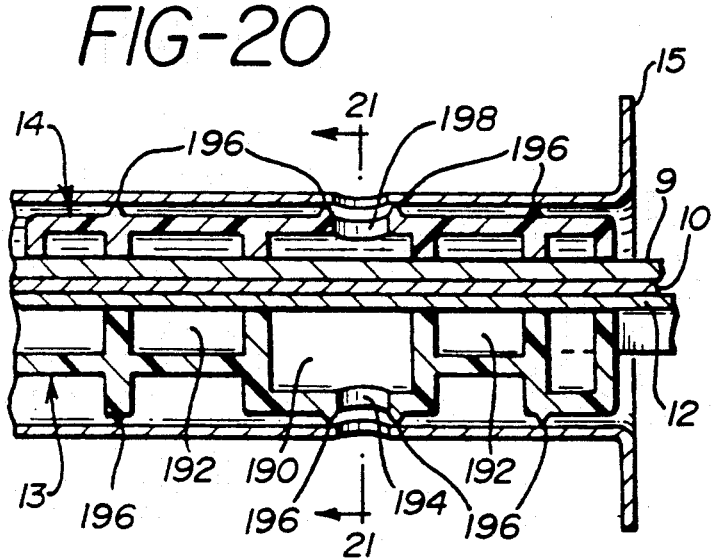
FIG. 20 is a partial cross-sectional view of the shaft assembly across lines 20—20 as seen in FIG. 1.
Figure 21:
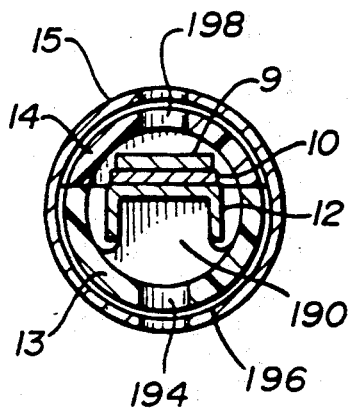
FIG. 21 is a cross-sectional view of FIG. 20 as seen across lines 21—21 of FIG. 20.

As seen in FIGS. 20 and 21, there is disclosed a sealing mechanism located near the proximal end of the shaft assembly of the endoscopic multiple clip applier. The sealing mechanism is circular in cross section and fits tightly through four crushed ribs 196 within the shaft support tube 15. Within the sealing mechanism are three chambers 190, 192 as identified in FIG. 20, through which the feeding and forming mechanisms of the instrument pass. The primary chamber 190 is an area through which a sealant fluid may be injected. Sealent may be inserted through insertion holes 194, 198. The outer or secondary chambers 192 are provided as spillover areas for the sealant. This is better seen in FIG. 20. The ends of the sealing mechanism are closed to prohibit the migration of sealant from the chambers 190 to the functional areas of the instrument.

The sealing system provides a cushioning mechanism to minimize instrument recoil during firing and retraction of trigger 25. This closed sealing mechanism also prevents the intraoperative gross loss of pressure through the instrument itself, while minimizing, through ribs 196, the possibility of instrument functional failure due to sealant migration. The system is sealed from outside the patient, and it is itself sealed from the moving parts of the instruments.

Figure 22A:
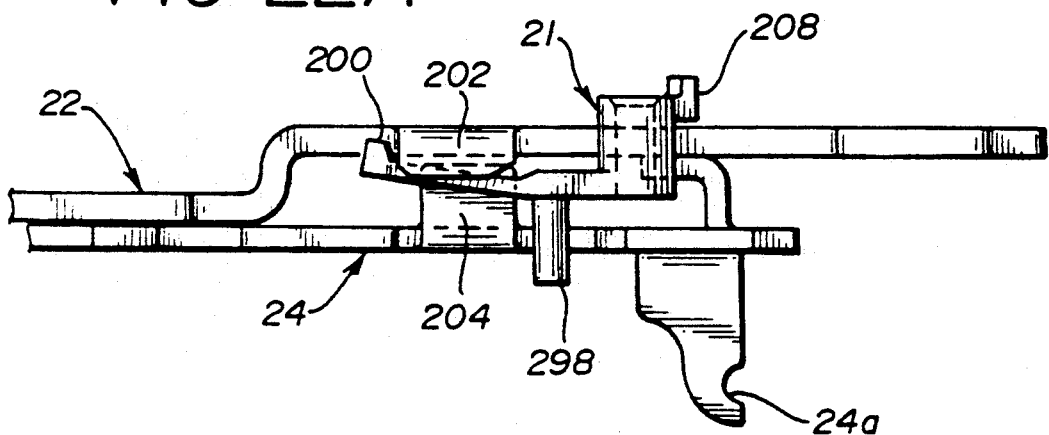
FIGS. 22A, 22B and 22C are sequential views of the clip feed timing mechanism of the invention.
Figure 22B:
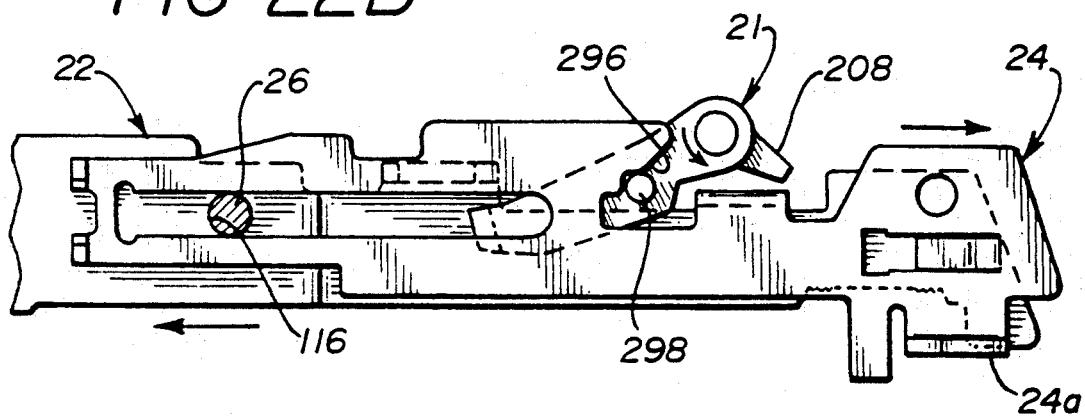
Figure 22C:
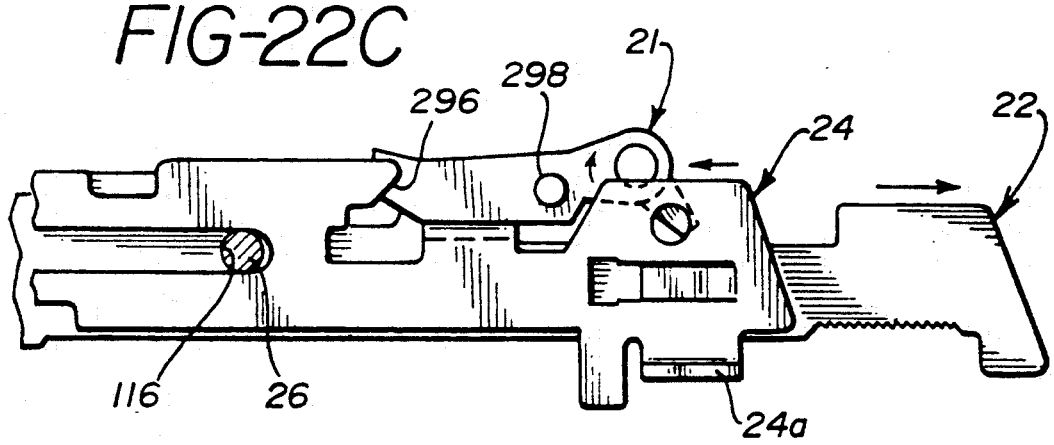

As seen in FIGS. 22A, 22B and 22C, the triggering system taken in conjunction with FIG. 5 consists of a precock trigger 21, which is pre-stressed and pivots on a post 206 into handle portion 16. Precock trigger 21 is biased so that there is eliminated any clearance between the precock trigger 21 and the former plate 22 located within the handles 16, 28. As the feeder plate 24 is retracted to the rear of the instrument away from the forming site (FIG. 22B), during handle actuation, a camming surface 296 on the feeder plate 24 contacts a cylindrical post 298 on the precock trigger 21. This causes the rotation of the precock trigger 21 into its precocked position as seen in FIG. 22B.

In its precocked position a projection 200 of the precock trigger 21 becomes locked behind a wall 202 extending from the former plate 22. The precock trigger 21 now blocks the path of a tab 204 extending from feeder plate 24. The feeder plate 24 cannot feed the next clip 8 into the jaws from this point until the timing wall 202 extending from the former plate 22 allows the precock trigger 21 to rotate out of the path of the feeder plate 24. This method of timing causes a sequencing operation for feeding clips which eliminates the possibility of feeding a second clip into the jaws 11 of the instrument in the event that the instrument is partially fired and re-opened.

As can be further seen in FIGS. 5 and 22C, torsion spring 20 connects to both lost motion lever mechanism 18 and anti back-up lever 19. The objective of the anti back-up lever 19 is to assure that a pressure is constantly maintained on the jaws 11 by cam channel 12 as the clip is being closed. Anti back-up lever 19 therefore causes cam channel 12 to be constantly urged forward. This prevents the clip 8 from falling out from the jaws 11a, 11b until the applier is fully actuated.

The system is actuated by rotation of the precock trigger 21, so that the tab 208 extending from the base of the precock trigger 21 into hole 210 of the lost motion lever 18 (and thus connected to the anti back-up lever 19 via torsion spring 20) acts as a toggle mechanism to engage and disengage the anti back-up lever 19. The hole width 210 of the lost motion lever 18 determines the relative motion of the precock trigger 21 and the lost motion lever 18. This allows timing of the anti back-up actuation mechanism to be adjusted in relation to the actuation of the precock trigger 21. The anti back-up lever 19 is constructed of a resilient material and has teeth 214 which engage the metallic teeth 212 on former plate 22, as seen in FIG. 5. The anti back-up lever 19 has a cam surface which tends to cam the teeth 214 away from former plate 22, in the event that the anti back-up mechanism must be overridden.

Figure 10:
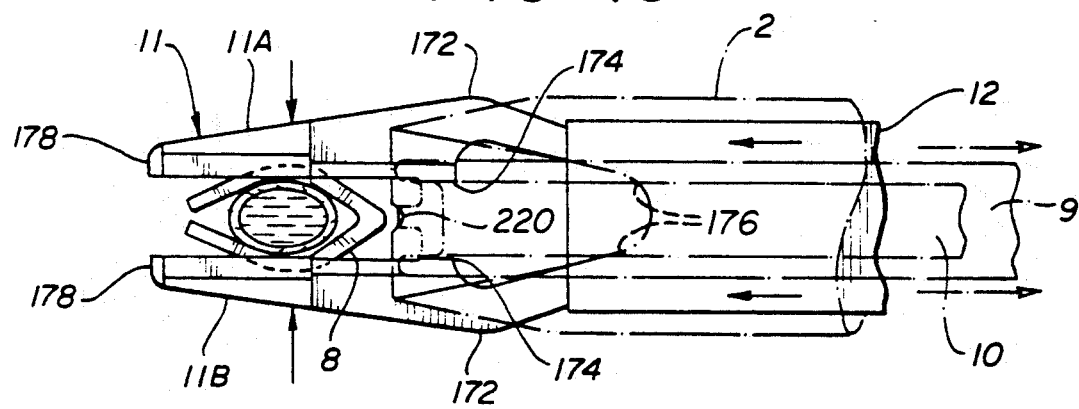
Figure 11:
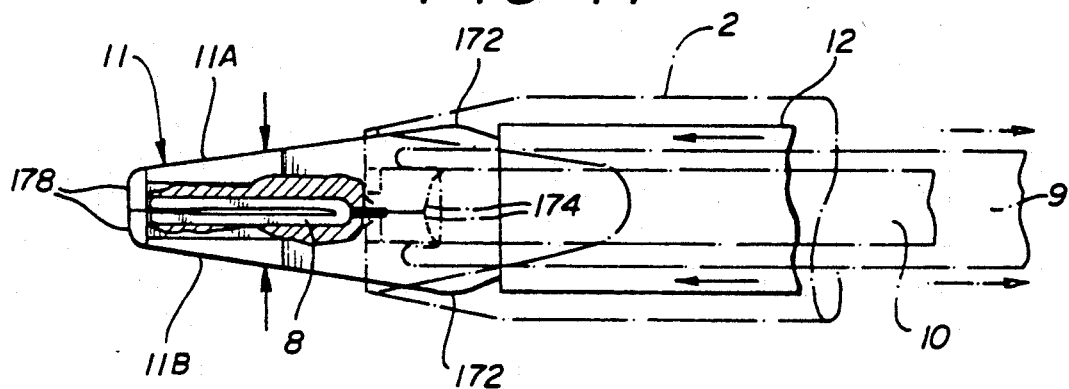

Finally, as seen FIGS. 9, 10 and 11, there is a tissue stop located as a V notch 220 in top shroud 2. This tissue stop is located near the rear end of the clip forming area within the jaws 11. As seen in FIG. 9, this maintains the clip 8 within the forming areas of the jaws 11 and guarantees proper gap size of the clips by insuring reliably proper placement of the forwardmost clip 8 within the jaw arms 11a, 11b. It also prevents the possibility of tissue damage by closing the clips too tightly. This feature promotes more secure clip closure and minimizes the possibility of damage to tissue.

Thus, as can be seen, in operation the mechanisms of this invention all function similarly, so that the system is able to operate a closure of a ligating clip about a blood vessel. The handle operates to actuate the jaws to close the clip. The various spring and trigger mechanisms operate to keep the clip adequately supported and provide enough force for closing. As has been described, there are numerous safety and redundant systems so that closure is assured. Therefore, while many objects and features have been described, the objects of the invention are to be understood as derived from the attached claims and their equivalents.

We claim:

1. An endoscopic mechanism comprising:
   an actuation mechanism;
   an endoscopic portion for insertion inside a body cavity having a proximal end and a distal end, said endoscopic portion including:
   a support tube with a tubular cross section, said support tube having an open distal end into which may pass fluids from said body cavity;
   a driving mechanism contained in said support tube and connected to said actuation mechanism at said endoscopic portion proximal end;
   a plurality of surgical fasteners in said support tube capable of being fastened to body tissue by said driving mechanism at said endoscopic portion distal end: and
   a venting mechanism including a passageway through the tubular cross section of said support tube proximally from the open distal end thereof providing communication between the interior of said support tube and the exterior thereof for venting body fluids which may have passed into said support tube through the open distal end thereof.

2. The mechanism of claim 1 wherein said passageway comprises a vent hole in said tubular cross-section and a channel between said vent hole and said distal end, wherein said channel provides a conduit between said vent hole and said distal end.

3. The mechanism of claim 2 further comprising a sealing mechanism at the proximal end of said endoscopic portion and said actuation mechanism and said driving mechanism extending through the sealing mechanism so that different ambient pressures may be maintained within said endoscopic portion and said actuation mechanism.

4. The mechanism of claim 3 wherein said sealing mechanism comprises a resilient sealant fitting within the tubular cross section of said endoscopic portion at its proximal end, with a plurality of chambers surrounded therein, said chamber providing communication between said actuation mechanism and said driving mechanism.

5. The mechanism of claim 1 comprising ligating clip applier wherein said surgical fasteners comprise a plurality of ligating clips each said clip having a pair of legs; and wherein said applier contains: a pair of jaws for closing one of said ligating clips, said jaws forming a part of said driving mechanism, and actuable by said actuation mechanism and a camming channel surrounding said jaws.

6. The applier of claim 5 including a feed bar containing a support mechanism for maintaining said clip on said jaws, said support mechanism including a pair of outer edges which contact said jaws, and a pair of angled protrusions which contact the legs of said clip.

7. The applier of claim 6 wherein said support mechanism operates in conjunction with a clip returning floor, said floor having a tab which remains in the plane of said clip throughout motion of said jaws, and said tab preventing proximal migration of said clip along said jaws.

8. The applier of claim 6 wherein said support mechanism maintains said jaws in a spaced-apart relationship with said clip between said jaws.

9. The applier of claim 5 wherein said camming channel has a camming surface which corresponds to a camming surface on each of said jaws such that the contact between said camming surfaces causes closure of said jaws.

10. The applier of claim 9 further including a tab within said camming channel which causes said jaws to open when said camming channel is caused to retract in said instrument by said actuation mechanism.

11. The applier of claim 9 further comprising each of said jaws having a distal end within which is held a said clip, and each of said jaw distal ends characterized by a point of contact with the distal end of said opposite jaw, and each said jaw containing an anti-torque post on said jaw, such that said clip may be held on said jaws between each of said jaw distal ends and each of said jaw anti-torque posts.

12. The applier of claim 11 further including a heel on each of said jaws spaced proximally from the corresponding jaw anti-torque post, each of said heels providing an additional point of contact between said jaws.

13. The applier of claim 11 wherein said jaws are held within a shroud, and said shroud having a distal surface in which to hold a blood vessel to be ligated.

14. The applier of claim 11 further including a feed bar forming a part of said driving mechanism, and operable along a path, wherein said clips are held in a stack and the first of said clips is moved from said clip stack to a position between said jaws due to retraction of said feed bar, and further including a lever which moves into the path of said feed bar after the last of said clips has been moved from said clip stack, thereby preventing operation of said feed bar.

15. The applier of claim 14 further including a spring-loaded feeder mechanism having a spring, wherein said lever is pivotably attached to said spring-loaded feeder mechanism, such that said lever is spring-loaded to be held out of the path of said feed bar by said feeder mechanism, such that when said feeder mechanism has moved the last of said clips on a clip stack, said feeder mechanism is inoperative to hold said spring of said feeder mechanism, thereby pivoting said lever into said feed bar path.

16. The endoscopic mechanism of claim 1 wherein said support tube is formed from torque resisting material which prevents deflection of said endoscopic mechanism along said tube during operation of said driving mechanism.

17. The endoscopic mechanism of claim 1 comprising a clip applier such that said fasteners are a plurality of clips on a clip stack and including: a pair of jaws for closing a said clip by operation of said driving mechanism; a transfer mechanism for moving a said clip from said clip stack a feed bar movable between said jaws and said clip stack, and a retaining member on said clip stack to hold said clips within said clip stack, such that said retaining member enables only one of said clips at a time to interact with said transfer mechanism.

18. The applier of claim 17 including a camming surface on said transfer mechanism, wherein said retaining member is moved into a retaining position by said camming surface, such that said retaining member prevents movement of said clips as said transfer mechanism returns to said clip stack in order to retrieve a said clip.

19. The applier of claim 17 further including a timing mechanism on said applier which causes loading of a clip onto said jaws when said jaws are opened to a maximum width, said timing mechanism comprising a blocking component attached to said transfer mechanism and said driving mechanism, such that said blocking component prevents operation of said transfer mechanism during operation of said driving mechanism to close said jaws.

20. The applier of claim 19 further including said timing mechanism interacting with said driving mechanism such that said driving mechanism is moved to a forwardmost position in order to close said jaws, and said driving mechanism prevented from reversing motion until said jaws have been closed on a said clip.

21. The applier of claim 17 wherein said clip stack is a unitary member of said clip applier.

22. A device for applying a plurality of surgical clips seriatim, said device comprising:
   an elongated shaft assembly containing a jaw member having a pair of spaced apart jaws for receiving a surgical clip therebetween, a clip feed mechanism for storing an array of surgical clips and delivering a clip between said jaws, and a jaw closure mechanism for closing a surgical clip positioned between said jaws; and
   a handle assembly connected to said shaft assembly containing a single trigger means for actuating said jaw closure mechanism to close a clip positioned in said jaws and for actuating said clip feed mechanism to deliver a clip between said jaws;
   said clip feed mechanism including A) an elongated clip track for housing said array of surgical clips in an end-to-end relationship in a first path extending through a first plane, B) spring means for shifting the distal-most clip in said first path out of the plane of said first path and into a second path extending through a second plane generally parallel to the plane of the first path, C) a feed bar member mounted for reciprocating movement in said shaft assembly in said second plane for (a) enabling said spring means to shift the distal-most clip in said first path from said first path into said second path upon proximal movement of said feed bar, and (b) contacting the distal-most clip and advancing same distally into a position between said jaws upon distal movement of said feed bar, and D) said clip track having an escapement member integral with said clip track that is movable between (a) a first position extending into said first path so as to engage the leading clip from the array and maintain the array of clips stationary within said first path as the distal-most clip is directed into said jaws, and (b) a second position wherein said escapement member is removed from said first path to allow distal movement of said array of clips.

23. The device as defined in claim 22 wherein the clip track is formed of an integral member having a rectangular cross-section defining a floor, lateral side walls, and a top overlying at least the legs of the clips.

24. The device as defined in claim 22, wherein said escapement member includes an escapement portion that is biased out of said first path toward said second position and is directed into said first path into said first position when said feed bar member contacts said end portion as it moves proximally.

25. The device as defined in claim 24 wherein said escapement portion is bent so as to extend distally and in a direction towards said first path so as to prevent distal movement of the array of clips in said first path.

26. The device as defined in claim 22 wherein said spring means includes a proximal end portion that is secured in said shaft assembly so as to preclude distal or proximal movement thereof and an intermediate portion that is movable between a first position extending into said second path to direct the distal clip thereinto and a second position located out of said second path, said intermediate portion of said spring means being biased toward its first position, said intermediate portion being movable into said second position in response to distal movement of said feed bar member.

27. The device as defined in claim 22 wherein the outer edge portions at the distal end of the feed bar are spaced by a dimension corresponding to the dimension between said spaced jaws and adapted to bear against said jaws as the distal-most clip is advanced between said jaws to prevent said jaws from closing until said feed bar member is withdrawn from between said jaws.

28. The device as defined in claim 27 wherein a distal end portion of said feed bar member contacts said clip positioned between said jaws and prevents proximal movement thereof.

29. A device for applying a plurality of surgical clips seriatim, said device comprising:
   an elongated shaft assembly containing a jaw member having a pair of spaced apart jaws for receiving a surgical clip therebetween a clip feed mechanism for storing an array of surgical clips and delivering a clip between said jaws, and a jaw closure mechanism for contacting said jaws and closing a surgical clip positioned between said jaws; and
   a handle assembly connected to said shaft assembly containing a single trigger means for actuating said jaw closure mechanism to close a clip positioned in said jaws and for actuating said clip feed mechanism to deliver a clip between said jaws;
   said jaw member includes a pair of spaced apart arms that define said jaws at a distal end portion thereof, each of said jaws having a distal portion and a proximal portion, said distal portions include a channel for receipt of a portion of a surgical clip therein, said channels having an end wall at the distal end thereof to thereby close said channels, said channels being in a generally parallel facing relationship to one another, said distal and proximal portions of said jaws having outer surfaces, said outer surfaces of said proximal portions defining outer cam surfaces that extend proximally and inwardly, said jaw closure mechanism including means for contacting said cam surfaces of said proximal portions as said jaw closure mechanism moves distally to cause said jaws to move towards one another and close a surgical clip positioned therebetween, said end walls of said channels have inner surfaces that contact one another as said jaws close the surgical clip, and said proximal portions have inner surfaces adjacent the proximal end of said cam surfaces that contact one another as said jaws close the surgical clip.

30. The device as defined in claim 24 in which said elongated shaft assembly has a substantially uniform external diameter throughout its length, and wherein the maximum width between the outer surfaces of said jaws in their open position is relatively the same as the external diameter of said elongated shaft assembly.

31. The device as defined in claim 24 wherein said elongated shaft assembly includes an outer tubular non-resilient member to provide resistance to bending.

32. The device as defined in claim 24 in which said jaw closure mechanism includes a cam channel having an integral jaw engaging mechanism, said jaw engaging mechanism forming a box-shaped element having a pair of lateral sides, a top and a bottom, said lateral sides capable of engaging said cam surfaces, and having folded members to complete said box, said folded members being joined by a dovetail joint.

33. The device as defined in claim 24 wherein each of said jaws includes inwardly extending projections located adjacent the distal end of said cam surfaces, said inwardly extending projections contact one another as the jaws close the surgical clip.

34. An instrument adapted for use in an insufflated body cavity comprising: an elongated tubular member having a distal working end containing an operating means adapted to be inserted into the body cavity and a proximal end adapted to be manipulated by a surgeon; at least one actuating element connecting said operating means and said proximal mounted for movement within said tubular member; means within said tubular member for sealing said tubular member against loss of gas from said insufflated body cavity, said sealing means including a housing within said tubular member between the distal and proximal ends thereof and disposed in sealed relationship with said tubular member and said actuating element; said housing including a sidewall, end walls, and divider walls which cooperate to define a central chamber and end chambers at opposite sides of said central chamber, said end and divider walls including clearance openings accommodating said actuating element, and means in said sidewalls for permitting sealant material to be inserted into said central chamber.

35. An instrument as defined in claim 34 in which said actuating element is mounted for reciprocating movement within said tubular member, and wherein the openings in said end walls and divider walls are aligned with one another to accommodate said actuating element.

36. In combination:
a surgical trocar including a tubular cannula having a given internal diameter; and
an endoscopic multiple clip applier comprising, an elongated shaft assembly including a jaw member having a pair of spaced apart jaws for receiving a surgical clip therebetween, said jaws extending outwardly from the distal end of said shaft assembly, said shaft assembly being generally cylindrical throughout its length and having an external diameter which permits said shaft assembly to be inserted into, and withdrawn from, said trocar cannula, a clip feed mechanism for storing an array of surgical clips within said elongated shaft assembly and for delivering a clip between said jaws, a jaw closure mechanism for moving said jaws from an open clip holding position to a closed clip closing position to apply a clip to body tissue, said jaws having a maximum width dimension between the outer surfaces in the open position that is no greater than the internal diameter of said trocar cannula and relatively the same as the outer diameter of said shaft assembly so that said shaft assembly with a clip positioned between said jaws can be inserted into, and withdrawn from, said trocar cannula without closing said jaws, and a handle assembly connected to said shaft assembly and containing a single trigger means operable to first actuate said jaw closure mechanism and close a clip positioned between said jaws and to thereafter automatically actuate said clip feeding mechanism to feed and position between said jaws the next clip from said array of clips.

37. A device for applying a plurality of surgical clips seriatim, said device comprising:
a) an elongated shaft assembly having an outer diameter including:
(i) a jaw member having at its distal portion a pair of spaced apart jaws for receiving a surgical clip between said jaws, said jaws being narrowly configured so that the greatest distance between the outer surfaces of said jaws at their fully open position is relatively the same as the outer diameter of said elongated shaft assembly, said jaws having channels in a generally parallel relationship for the receipt of a surgical clip therein, and said jaw member including a pair of proximally extending spaced apart jaw arms, said jaw arms each having a primary heel located proximally of said jaws that is defined as an inner surface in each jaw arm which contacts the corresponding inner surface in the opposite jaw arm as the jaws close a surgical clip;
(ii) a clip feed mechanism for storing an array of surgical clips and delivering a clip between said jaws, said clip feed mechanism including: (A) an elongated clip track for housing said array or surgical clips in a first path extending through a first plane with said clips arranged end-to-end with their legs facing the distal end of the device, (B) spring means for shifting the distal-most clip in said first path out of the plane of said first path and into a second path extending through a second plane generally parallel to the plane of the first path, (C) a feed bar member positioned in said second plane such that proximal movement of said feed bar member enables said spring means to shift said distal-most clip in said first path from said first path into said second path and such that distal movement of said feed bar member advances said distal-most clip into a position between said jaws, (D) an escapement member associated with said clip track which is movable between (1) a first position extending into said first path so as to maintain the array of clips stationary within said first path, and (2) a second position wherein said escapement member is removed from said first path to allow distal movement of said array of clips;
(iii) a jaw closure mechanism for closing a surgical clip positioned between said jaws including a cam channel having an integral jaw engaging mechanism, said cam channel including a box-shaped element with a pair of lateral sides, a top and a bottom, said lateral sides capable of engaging the outer surfaces of the proximal portions of said jaws and said top having a folded member to complete said box, said folded member being formed as a dovetail joint;
(iv) a gaseous sealing structure comprising a housing which includes a sidewall, endwalls and divider walls which cooperate to define a central chamber, and end chambers at opposite ends of said central chamber, said end and divider walls including clearance openings for accommodating movement of said clip feed mechanism and said jaw closure mechanism, said sidewall having apertures for permitting sealant material to be inserted into said central chamber; and (b) a handle assembly connected to said shaft assembly containing a single trigger means for actuating said jaw cam channel to close a clip positioned in said jaws and for actuating the distal and proximal movements of said feed bar member to deliver a clip between said jaws.

38. The device as defined in claim 37 wherein said elongated shaft assembly includes an outer non-resilient tube to provide resistance to bending.

39. The device as defined in claim 37 wherein the distal end of said feed bar member is dimensioned such that the width of said feed bar member is approximately the same as the width of said clips.

40. The device as defined in claim 37 wherein the distal end of said feed bar member is configured to contact the distal-most clip at the outer edges of said clip.

41. The device as defined in claim 37 wherein the outer surfaces of the distal end of said feed bar member bear against the inner surfaces of said jaws to prevent said jaws from closing when a clip is positioned in said jaws.

42. The device as defined in claim 37 wherein said clip track is comprised of a one-piece channel having a generally rectilinear cross-section dimensioned to prevent misalignment of surgical clips in said array of surgical clips.

43. The device as defined in claim 37 wherein said elongated shaft assembly contains openings distal to said gaseous sealing structure to allow the passage of fluids into and out of the elongated shaft.

44. The device as defined in claim 37 wherein each of said channels having an end wall at a distal end thereof to close said channels, said end walls having inner surfaces that contact one another as the jaws close a surgical clip.

* * * * *

UNITED STATES PATENT AND TRADEMARK OFFICE
CERTIFICATE OF CORRECTION

PATENT NO. : 5,171,249
DATED : December 15, 1992
INVENTOR(S) : David Stefanchik et al.

It is certified that error appears in the above-identified patent and that said Letters Patent is hereby corrected as shown below:

In Column 15, Claim 34, Line 25, after "proximal" insert -- end --.

In Column 16, Claim 37, Line 33, "or" should read -- of --.

Signed and Sealed this

Ninth Day of November, 1993

*Attest:*

BRUCE LEHMAN

*Attesting Officer*  *Commissioner of Patents and Trademarks*